United States Patent
Ross et al.

[11] Patent Number: 5,886,015
[45] Date of Patent: Mar. 23, 1999

[54] BENZYLOXY SUBSTITUTED AROMATICS AND THEIR USE AS FUNGICIDES AND INSECTICIDES

[75] Inventors: Ronald Ross, Jamison; Ted Tsutomu Fujimoto, Churchville; Steven Howard Shaber, Horsham, all of Pa.

[73] Assignee: Rohm and Haas Company, Philadelphia, Pa.

[21] Appl. No.: 867,376

[22] Filed: Jun. 2, 1997

[51] Int. Cl.⁶ .................... A61K 31/42; A61K 31/415; C07D 231/10; C07D 261/06

[52] U.S. Cl. .................... 514/378; 514/403; 514/406; 548/375.1; 548/379.4; 548/247; 548/240

[58] Field of Search .................. 548/375.1, 379.4, 548/247, 240; 514/378, 403, 406

[56] References Cited

U.S. PATENT DOCUMENTS

| | | | |
|---|---|---|---|
| 5,185,342 | 2/1993 | Hayase et al. | 514/274 |
| 5,403,838 | 4/1995 | Kirsten et al. | 514/224.2 |

FOREIGN PATENT DOCUMENTS

| | | |
|---|---|---|
| 0278595 A2 | 8/1988 | European Pat. Off. . |
| 335519 A1 | 10/1989 | European Pat. Off. . |
| 0398692 A2 | 11/1990 | European Pat. Off. . |
| 0474042 A1 | 3/1992 | European Pat. Off. . |

*Primary Examiner*—Deborah C. Lambkin
*Attorney, Agent, or Firm*—Guy T. Donatiello

[57] ABSTRACT

Compounds with fungicidal and insecticidal properties having formula

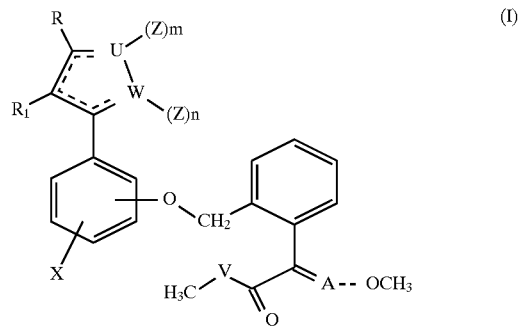

(I)

wherein A is N or CH; V is O or NH;
m and n are independently 0 and 1 provided that m+n is not 2, and U and W are independently O or N;
such that when U and W are both N and n is 0 and m is 1, the bond between the 1 and 5 atoms is a double bond and the bond between the $C_3$–$C_4$ atoms is a single or double bond, and when n is 1 and m is 0, the bond between the 2 and 3 atoms is a double bond and the bond between the $C_4$–$C_5$ atoms is a single or double bond;
and that when U is O and W is N and n=m=0, the bond between the 1 and 5 atoms is a double bond and the bond between the $C_3$–$C_4$ atoms is a single or double bond;
and that when U is N and W is O and n=m=0, the bond between the 2 and 3 atoms is a double bond and the bond between the $C_4$–$C_5$ atoms is a single or double bond;
X is independently selected from hydrogen, halo, ($C_1$–$C_4$) alkyl, and $C_1$–$C_4$)alkoxy;
R is independently selected from hydrogen, ($C_1$–$C_{12}$)alkyl, halo($C_1$–$C_{12}$)alkyl, ($C_2$–$C_8$)alkenyl, ($C_2$–$C_8$)alkynyl ($C_1$–$C_{12}$)alkoxy($C_1$–$C_{12}$)alkyl, ($C_3$–$C_7$)cycloalkyl, ($C_3$–$C_7$)cycloalkyl($C_1$–$C_4$)alkyl, aryl, aralkyl, heterocyclic and
$R_1$ is independently selected from hydrogen, ($C_1$–$C_6$)alkyl, and aryl; and
Z is selected from ($C_1$–$C_6$)alkyl, halo($C_1$–$C_6$)alkyl, ($C_3$–$C_7$) cycloalkyl, ($C_3$–$C_7$)cycloalkyl($C_1$–$C_4$)alkyl, aryl and aralkyl.

20 Claims, No Drawings

BENZYLOXY SUBSTITUTED AROMATICS AND THEIR USE AS FUNGICIDES AND INSECTICIDES

The present invention relates to benzyloxy substituted-phenyl compounds, compositions containing these compounds and methods for controlling fungi and insects by the use of a fungitoxic and insecticidal amount of these compounds.

It is known that propenoic acids and oxime ethers of certain benzyloxy substituted phenyl compounds are useful as fungicides. The substitution of the phenyl ring big certain heterocycles is known in the art (see for example U.S. Pat. No. 5,185,342)

We have discovered phenyl derivatives which possess a five membered ring heterocycle. These novel compositions also possess fungicidal and insecticidal properties.

The novel benzyloxy substitutedphenyl compounds of the present invention have the Formula (I)

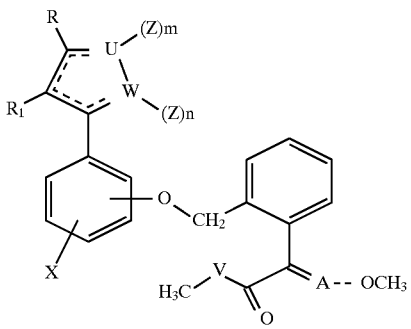

wherein A is N or CH; V is O or NH;
m and n are independently 0 and 1 provided that m+n is not 2, and U and W are independently O or N;
such that when U and W are both N and n is 0 and m is 1, the bond between the 1 and 5 atoms is a double bond and the bond between the C3–C4 atoms is a single or double bond, and when n is 1 and m is 0, the bond between the 2 and 3 atoms is a double bond and the bond between the C4–C5 atoms is a single or double bond;
and that when U is O and W is N and n=m=0, the bond between the 1 and 5 atoms is a double bond and the bond between the C3–C4 atoms is a single or double bond;
and that when U is N and W is O and n=m=0, the bond between the 2 and 3 atoms is a double bond and the bond between the C4–C5 atoms is a single or double bond;
X is independently selected from hydrogen, halo, $(C_1-C_4)$ alkyl, and $C_1-C_4$)alkoxy;
R is independently selected from hydrogen, $(C_1-C_{12})$alkyl, halo$(C_1-C_{12})$alkyl, $(C_2-C_8)$alkenyl, $(C_2-C_8)$alkynyl, $(C_1-C_{12})$alkoxy$(C_1-C_{12})$alkyl, $(C_3-C_7)$cycloalkyl, $(C_3-C_7)$cyctoalkyl$(C_1-C_4)$alkyl, aryl, aralkyl, heterocyclic; and
$R_1$ is independently selected hydrogen, $(C_1-C_6)$alkyl, and aryl;
Z is selected from $(C_1-C_6)$alkyl, halo$(C_1-C_6)$alkyl, $(C_3-C_7)$ cycloalkyl, $(C_3-C_7)$cycloalkyl$(C_{1-C4})$alkyl, aryl, aralkyl.

The aforementioned $(C_1-C_{12})$alkyl, $(C_1-C_2)$alkoxy, $(C_2-C_8)$alkenyl, $(C_2-C_8)$ alkynyl and $(C_3-C_7)$cycloalkyl groups may be optionally substituted with up to three substituents selected from the group consisting of halogen, nitro, trihalomethyl and cyano.

The term alkyl includes both branched and straight chained alkyl groups from 1 to 12 carbon atoms. Typical alkyl groups are methyl, ethyl, n-propyl, isopropyl, n-butyl, sec-butyl, isobutyl, t-butyl, n-pentyl, isopentyl, n-hexyl, n-heptyl, isooctyl, nonyl, decyl, undecyl, dodecyl and the like. The term haloalkyl refers to an alkyl group substituted with 1 to 3 halogens.

The term alkenyl refers to an ethylenically unsaturated hydrocarbon group, straight or branched, having a chain length of 2 to 12 carbon atoms and 1 or 2 ethylenic bonds. The term haloalkenyl refers to an alkenyl group substitued with 1 to 3 halogen atoms. The term alkynyl refers to an unsaturated hydrocarbon group, straight or branched, having a chain length of 2 to 12 carbon atoms and 1 or 2 acetylenic bonds.

The term cycloalkyl refers to a saturated ring system having 3 to 7 carbon atoms.

The term aryl is understood to be plhenyl or napthyl, which is optionally substituted with up to three substituents selected from the group consisting of halogen, cyano, nitro, trihalomethyl, phenyl, phenoxy, $(C_1-C_4)$alkyl, $(C_1-C_4)$ alkylthio, $(C_1-C_4)$alkylsulfoxide $(C_1-C_6)$alkoxy and halo $(C_1-C_4)$alkyl.

Typical aryl substituents include but are not limited to 4-chlorophenyl, 4-fluorophenyl, 4-bromnophenyl, 2-nmethoxyphenyt, 2-methylpllenyl, 3-methyphenyl, 4-methylphenyl, 2,4-dibromophenyl, 3,5-difluolroplhenyl, 2,4,6-trichlorophenyl, 4-methoxyphenyl, 2-chloronapthyl, 2,4-dimethoxyphenyl, 4-(trifluoromethyl)phenyl and 2-iodo-4-methylphenyl.

The term heterocyclic refers to a substituted or unsubstituted 5 or 6 membered unsaturated ring containing one, two or three heteroatoms, preferably one or two heteroatoms selected from oxygen, nitrogen and sulfur; or is a bicyclic unsaturated ring system containing up to 10 atoms including one heteratom selected from oxygen, nitrogen and sulfur. Examples of heterocycles includes, but is not limited to, 2-, 3- or 4-pyridinyl, pyrazinyl, 2-, 4-, or 5-pyrimidinyl, pyridazinyl, triazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl and isoquinolyl. The heterocyclic ring may be optionally substituted with up to two substituents independently selected from $(C_1-C_4)$alkyl, halogen, cyano, nitro and trihalomethyl.

The term aralkyl is used to describe a group wherein the the alkyl chain is from 1 to 10 carbon atoms and can be branched or straight chain, preferably a straight chain, with a terminal aryl portion, as defined above. Typical aralkyl moieties include, but are not limited to, optionally substituted benzyl, phenethyl, phenpropyl and phenbutyl moieties. Typical benzyl moieties are 2-chlorobenzyl, 3-chlorobenzyl, 4-chlorobenzyl, 2-fluorobenzyl, 3-fluorobenzyl, 4-fluorobenzyl, 4-trifluoromethylbenzyl, 2,4-dichlorobenzyl, 2,4-dibromobenzyl, 2-methylbenzyl, 3-methylbenzyl, and 4-methylbenzyl. Typical phenethyl moieties are 2-(2-chlorophenyl)ethyl, 2-(3-chloroplhenyl) ethyl, 2-(4-chloroplhenyl)ethyl, 2-(2-fluorophenyl)ethyl, 2-(3-fluorophenyl)ethyl, 2-(4-fluoro-phenyl)ethyl, 2-(2-methylphenyl)ethyl, 2-(3-methylphenyl)ethyl, 2-(4-methylphenyl)ethyl, 2-(4-trifluoromnethylphenyl)ethyl, 2-(2-methoxyphenyl)ethyl, 2-(3-methoxyphenyl)ethyl, 2-(4-methoxyphenyl)ethyl, 2-(2,4-dichlorophenyl)ethyl, 2-(3,5-dinmethoxyphenyl)ethyl. Typical phenpropyl moieties are 3-phenylpropyl, 3-(2-chloro-phenyl)propyl, 3-(3-chlorophenyl)propyl, 3-(4-chlorophenyl)propyl, 3-(2,4-dichloro-phenyl)propyl, 3-(2-fluorophenyl)propyl, 3-(3- fluorophenyl)propyl, 3-(4-fluorophenyl)-propyl, 3-(2-methylphenyl)propyl, 3-(3-methylphenyl)propyl, 3-(4-methylphenyl)-ethyl, 3-(2-methoxyphenyl)propyl, 3-(3-mnethoxyphenyl)propyl, 3-(4-methoxyphenyl) propyl, 3-(4-trifluoromethylphenyl)propyl, 3-(2,4-dichlorophenyl)propyl and 3-(3,5-dimethoxyphenyl)propyl. Typical phenbutyl moities include are 4-phenylbutyl, 4-(2-chloroplienyl)butyl, 4-(3-chlorophenyl)butyl, 4-(4-chlorophenyl)butyl, 4-(2-fluorophenyl)butyl, 4-(3-fluorophenyl)butyl, 4-(4-fluorophenyl)butyl, 4-(2-methylphenyl)butyl, 4-(3-methylphenyl)butyl, 4-(4-methylphenyl)butyl, 4-(2,4-dichlorophenyl)butyl, 4-(2-methoxyphenyl)butyl, 4-(3-methoxyphenyl)butyl and 4-(4-niethoxy-phenyl)butyl.

Halogen or halo is meant to include iodo, fluoro, bromo and chloro moieties.

Because of the C=C or C=N double bonds the novel compounds of the general Formula I mnay be obtained in preparation as E/Z isomeric mixtures. These isomers can be separated into individual components by conventional means. The pyrazolines and isoxazolines of Formula I may be obtained in preparation as cis and trans isomeric mixtures. These isomers can be separated into individual components by conventional means. Both the individual isomeric compounds and mixtures thereof form subjects of the invention and can be used as fungicides.

A preferred embodiment of this invention are the compounds, enantiomorphs, salts and complexes of Formula (I) when R is $(C_1-C_{12})$alkyl; phenyl substituted with preferably one or two substituents independently selected from halo, trihalomethyl, cyano, $(C_1-C_4)$alkyl, $(C_1-C_4)$alkylthio, $(C_1-C_4)$alkoxy; or phenyl, $R_1$ is H, where the $OCH_2$(2-substitutedphenyl) moiety is bonded at the meta position to the 5-menmbered ring substituent of the phenyl ring as shown in Formula I'.

A more preferred embodiment of this invention are the compounds, enantiomorphs, salts and complexes of Formula (I) is when X is hydrogen and R is halophenyl and A is CH and V is O. The preferred geometry when A is CH or N is the E isomer.

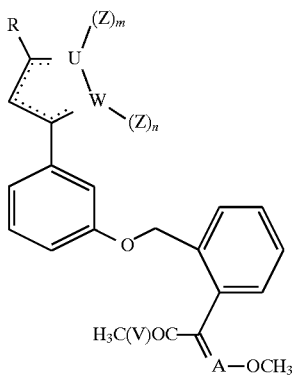

Typical compounds encompassed by the present invention of Formula I include those compounds presented in Table 1 of Formula II, III and IV where X=H, $R_1$=H, U and W are N and n=0 and m=1.

TABLE 1

| Cmpd# | R | Formula | Z | A | V |
|---|---|---|---|---|---|
| 1.01 | Ar | II | $CH_3$ | CH | O |
| 1.02 | Ar | III | $CH_3$ | CH | O |
| 1.03 | Ar | IV | $CH_3$ | CH | O |
| 1.04 | 4-Cl(Ar) | II | $CH_3$ | CH | O |
| 1.05 | 4-Cl(Ar) | III | $CH_3$ | CH | O |
| 1.06 | 4-Cl(Ar) | IV | $CH_3$ | CH | O |
| 1.07 | 4-F(Ar) | II | $CH_3$ | CH | O |
| 1.08 | 4-F(Ar) | III | $CH_3$ | CH | O |
| 1.09 | 4-F(Ar) | IV | $CH_3$ | CH | O |
| 1.10 | 2-$CH_3$(Ar) | II | $CH_3$ | CH | O |
| 1.11 | 2-$CH_3$(Ar) | III | $CH_3$ | CH | O |
| 1.12 | 2-$CH_3$(Ar) | IV | $CH_3$ | CH | O |
| 1.13 | 4-$CH_3$(Ar) | II | $CH_3$ | CH | O |
| 1.14 | 4-$CH_3$(Ar) | III | $CH_3$ | CH | O |
| 1.15 | 4-$CH_3$(Ar) | IV | $CH_3$ | CH | O |
| 1.16 | 4-$CF_3$(Ar) | II | $CH_3$ | CH | O |
| 1.17 | 2,4-Cl(Ar) | II | $CH_3$ | CH | O |
| 1.18 | $CH_3$ | II | $CH_3$ | CH | O |
| 1.19 | $CH_2CH_3$ | II | $CH_3$ | CH | O |
| 1.20 | $CH_2CH_2CH_3$ | II | $CH_3$ | CH | O |
| 1.21 | $CH(CH_3)_2$ | II | $CH_3$ | CH | O |
| 1.22 | $CH_2(CH_2)_3CH_3$ | II | $CH_3$ | CH | O |
| 1.23 | $CH_2(CH_2)_4CH_3$ | II | $CH_3$ | CH | O |
| 1.24 | $CH_2CH(CH_3)_2$ | II | $CH_3$ | CH | O |
| 1.25 | $CH(CH_3)CH_2CH_3$ | II | $CH_3$ | CH | O |
| 1.26 | $C(CH_3)_3$ | II | $CH_3$ | CH | O |
| 1.27 | $CH_2C(CH_3)_3$ | II | $CH_3$ | CH | O |
| 1.28 | $CH(CH_3)CH_2CH_2CH_3$ | II | $CH_3$ | CH | O |
| 1.29 | $C(CH_3)_2CH_2CH_3$ | II | $CH_3$ | CH | O |
| 1.30 | $CF_3$ | II | $CH_3$ | CH | O |
| 1.31 | $CF_2CF_3$ | II | $CH_3$ | CH | O |

TABLE 1-continued

| | | | | | |
|---|---|---|---|---|---|
| 1.32 | $CH_2CF_3$ | II | $CH_3$ | CH | O |
| 1.33 | $CH=CH_2$ | II | $CH_3$ | CH | O |
| 1.34 | cyclopropyl | II | $CH_3$ | CH | O |
| 1.35 | cyclopentyl | II | $CH_3$ | CH | O |
| 1.36 | cyclohexyl | II | $CH_3$ | CH | O |
| 1.37 | $CH_2OCH_3$ | II | $CH_3$ | CH | O |
| 1.38 | $CH_2OCH_2CH_3$ | II | $CH_3$ | CH | O |
| 1.39 | $CH_2CH_2OCOAr$ | II | $CH_3$ | CH | O |
| 1.40 | $CH_2OCH_2Ar$ | II | $CH_3$ | CH | O |
| 1.41 | 2-pyridyl | II | $CH_3$ | CH | O |
| 1.42 | 3-pyridyl | II | $CH_3$ | CH | O |
| 1.43 | 2-pyrimidyl | II | $CH_3$ | CH | O |
| 1.44 | 4-pyrimidyl | II | $CH_3$ | CH | O |
| 1.45 | 2-thienyl | II | $CH_3$ | CH | O |
| 1.46 | 3-thienyl | II | $CH_3$ | CH | O |
| 1.47 | 2-napthyl | II | $CH_3$ | CH | O |
| 1.48 | Ar | II | $C_2H_5$ | CH | O |
| 1.49 | 4-Cl(Ar) | II | $C_2H_5$ | CH | O |
| 1.50 | $CH_3$ | II | $C_2H_5$ | CH | O |
| 1.51 | $CH_2CH_3$ | II | $C_2H_5$ | CH | O |
| 1.52 | $CH_2CH_2CH_3$ | II | $C_2H_5$ | CH | O |
| 1.53 | $CH(CH_3)_2$ | II | $C_2H_5$ | CH | O |
| 1.54 | $CH_2(CH_2)_3CH_3$ | II | $C_2H_5$ | CH | O |
| 1.55 | $CH_2CH(CH_3)_2$ | II | $C_2H_5$ | CH | O |
| 1.56 | $C(CH_3)_3$ | II | $C_2H_5$ | CH | O |
| 1.57 | Ar | III | 4-Cl(Ar) | CH | O |
| 1.58 | Ar | II | $CH_2CH_2CH_3$ | CH | O |
| 1.59 | $CH_3$ | II | $CH_2CH_2CH_3$ | CH | O |
| 1.60 | $CH_2CH_2CH_3$ | II | $CH_2CH_2CH_3$ | CH | O |
| 1.61 | $CH(CH_3)_2$ | II | $CH_2CH_2CH_3$ | CH | O |
| 1.62 | $CH_2(CH_2)_3CH_3$ | II | $CH_2CH_2CH_3$ | CH | O |
| 1.63 | $CH_2CH(CH_3)_2$ | II | $CH_2CH_2CH_3$ | CH | O |
| 1.64 | $C(CH_3)_3$ | II | $CH_2CH_2CH_3$ | CH | O |
| 1.65 | 2-pyridyl | II | $CH_2CH_2CH_3$ | CH | O |
| 1.66 | 3-pyridyl | II | $CH_2CH_2CH_3$ | CH | O |
| 1.67 | 4-pyrimidyl | II | $CH_2CH_2CH_3$ | CH | O |
| 1.68 | 2-thienyl | II | $CH_2CH_2CH_3$ | CH | O |
| 1.69 | 3-thienyl | II | $CH_2CH_2CH_3$ | CH | O |
| 1.70 | 2-napthyl | II | $CH_2CH_2CH_3$ | CH | O |

Further typical compounds described by the present invention are described in the following tables.
Table 2:
Compounds 2.1 to 2.47 are Conpounds of Table 1 of Formula II, III, IV where Z is Ar.
Table 3:
Compounds 3.1 to 3.47 are Compounds of Table 1 of Formula II, III, IV where Z is $CH_2Ar$.
Table 4:
Compounds 4.1 to 4.47 are Compounds of Table 1 of Formula II, III, IV where Z is $CH_2CF_3$.
Table 5:
Compounds 5.1 to 5.47 are Compounds of Table 2 of Formula II, III, IV where V=O and A is N.
Table 6:
Compounds 6.1 to 6.47 are Compounds of Table 2 of Formula II, III, IV where V=NH and A is N.
Table 7:
Compounds 7.1 to 7.47 are Compounds of Table 3 of Formula II, III, IV where V=O and A is N.
Table 8:
Compounds 8.1 to 7.47 are Compounds of Table 3 of Formula II, III, IV where V=NH and A is N.
Table 9:
Compounds 9.1 to 9.47 are Compounds of Table 4 of Formula II, III, IV where V=O and A is N.
Table 10:
Compounds 10.1 to 10.47 are Compounds of Table 4 of Formula II, III, IV where V=NH and A is N.
Typical compounds encompassed by the present invention of Formula I include those compounds presented in Table 11 of Formula V, VI and VII where X=H, $R_1$=H, U and W are N and n=1 and m=0.

TABLE 11

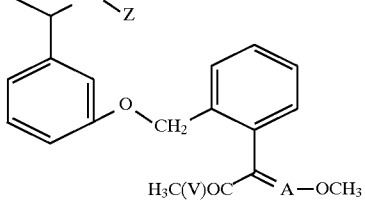
(V)

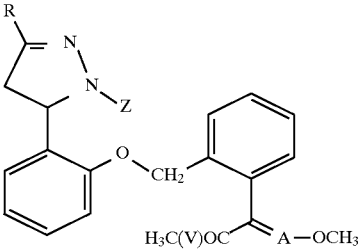
(VI)

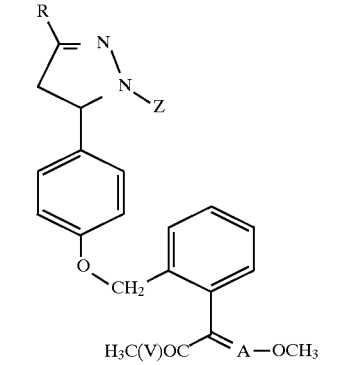
(VII)

| Cmpd# | R | Formula | Z | A | V |
|---|---|---|---|---|---|
| 11.01 | Ar | V | $CH_3$ | CH | O |
| 11.02 | Ar | VI | $CH_3$ | CH | O |
| 11.03 | Ar | VII | $CH_3$ | CH | O |
| 11.04 | 4-Cl(Ar) | V | $CH_3$ | CH | O |
| 11.05 | 4-Cl(Ar) | VI | $CH_3$ | CH | O |
| 11.06 | 4-Cl(Ar) | VII | $CH_3$ | CH | O |
| 11.07 | 4-F(Ar) | V | $CH_3$ | CH | O |
| 11.08 | 4-F(Ar) | VI | $CH_3$ | CH | O |
| 11.09 | 4-F(Ar) | VII | $CH_3$ | CH | O |
| 11.10 | 2-$CH_3$(Ar) | V | $CH_3$ | CH | O |
| 11.11 | 2-$CH_3$(Ar) | VI | $CH_3$ | CH | O |
| 11.12 | 2-$CH_3$(Ar) | VII | $CH_3$ | CH | O |
| 11.13 | 4-$CH_3$(Ar) | V | $CH_3$ | CH | O |
| 11.14 | 4-$CH_3$(Ar) | VI | $CH_3$ | CH | O |
| 11.15 | 4-$CH_3$(Ar) | VII | $CH_3$ | CH | O |
| 11.16 | 4-$CF_3$(Ar) | V | $CH_3$ | CH | O |
| 11.17 | 2,4-Cl(Ar) | V | $CH_3$ | CH | O |
| 11.18 | $CH_3$ | V | $CH_3$ | CH | O |
| 11.19 | $CH_2CH_3$ | V | $CH_3$ | CH | O |
| 11.20 | $CH_2CH_2CH_3$ | V | $CH_3$ | CH | O |
| 11.21 | $CH(CH_3)_2$ | V | $CH_3$ | CH | O |
| 11.22 | $CH_2(CH_2)_3CH_3$ | V | $CH_3$ | CH | O |
| 11.23 | $CH_2(CH_2)_4CH_3$ | V | $CH_3$ | CH | O |
| 11.24 | $CH_2CH(CH_3)_2$ | V | $CH_3$ | CH | O |
| 11.25 | $CH(CH_3)CH_2CH_3$ | V | $CH_3$ | CH | O |
| 11.26 | $C(CH_3)_3$ | V | $CH_3$ | CH | O |
| 11.27 | $CH_2C(CH_3)_3$ | V | $CH_3$ | CH | O |
| 11.28 | $CH(CH_3)CH_2CH_2CH_3$ | V | $CH_3$ | CH | O |
| 11.29 | $C(CH_3)_2CH_2CH_3$ | V | $CH_3$ | CH | O |

TABLE 11-continued

| | | | | | |
|---|---|---|---|---|---|
| 11.30 | CF$_3$ | V | CH$_3$ | CH | O |
| 11.31 | CF$_2$CF$_3$ | V | CH$_3$ | CH | O |
| 11.32 | CH$_2$CF$_3$ | V | CH$_3$ | CH | O |
| 11.33 | CH=CH$_2$ | V | CH$_3$ | CH | O |
| 11.34 | cyclopropyl | V | CH$_3$ | CH | O |
| 11.35 | cyclopentyl | V | CH$_3$ | CH | O |
| 11.36 | cyclohexyl | V | CH$_3$ | CH | O |
| 11.37 | CH$_2$OCH$_3$ | V | CH$_3$ | CH | O |
| 11.38 | CH$_2$OCH$_2$CH$_3$ | V | CH$_3$ | CH | O |
| 11.39 | CH$_2$CH$_2$OCOAr | V | CH$_3$ | CH | O |
| 11.40 | CH$_2$OCH$_2$Ar | V | CH$_3$ | CH | O |
| 11.41 | 2-pyridyl | V | CH$_3$ | CH | O |
| 11.42 | 3-pyridyl | V | CH$_3$ | CH | O |
| 11.43 | 2-pyrimidyl | V | CH$_3$ | CH | O |
| 11.44 | 4-pyrimidyl | V | CH$_3$ | CH | O |
| 11.45 | 2-thienyl | V | CH$_3$ | CH | O |
| 11.46 | 3-thienyl | V | CH$_3$ | CH | O |
| 11.47 | 2-napthyl | V | CH$_3$ | CH | O |
| 11.48 | Ar | V | C$_2$H$_5$ | CH | O |
| 11.49 | 4-Cl(Ar) | V | C$_2$H$_5$ | CH | O |
| 11.50 | CH$_3$ | V | C$_2$H$_5$ | CH | O |
| 11.51 | CH$_2$CH$_3$ | V | C$_2$H$_5$ | CH | O |
| 11.52 | CH$_2$CH$_2$CH$_3$ | V | C$_2$H$_5$ | CH | O |
| 11.53 | CH(CH$_3$)$_2$ | V | C$_2$H$_5$ | CH | O |
| 11.54 | CH$_2$(CH$_2$)$_3$CH$_3$ | V | C$_2$H$_5$ | CH | O |
| 11.55 | CH$_2$CH(CH$_3$)$_2$ | V | C$_2$H$_5$ | CH | O |
| 11.56 | C(CH$_3$)$_3$ | V | C$_2$H$_5$ | CH | O |
| 11.57 | Ar | VI | 4-Cl(Ar) | CH | O |
| 11.58 | Ar | V | CH$_2$CH$_2$CH$_3$ | CH | O |
| 11.59 | CH$_3$ | V | CH$_2$CH$_2$CH$_3$ | CH | O |
| 11.60 | CH$_2$CH$_2$CH$_3$ | V | CH$_2$CH$_2$CH$_3$ | CH | O |
| 11.61 | CH(CH$_3$)$_2$ | V | CH$_2$CH$_2$CH$_3$ | CH | O |
| 11.62 | CH$_2$(CH$_2$)$_3$CH$_3$ | V | CH$_2$CH$_2$CH$_3$ | CH | O |
| 11.63 | CH$_2$CH(CH$_3$)$_2$ | V | CH$_2$CH$_2$CH$_3$ | CH | O |
| 11.64 | C(CH$_3$)$_3$ | V | CH$_2$CH$_2$CH$_3$ | CH | O |
| 11.65 | 2-pyridyl | V | CH$_2$CH$_2$CH$_3$ | CH | O |
| 11.66 | 3-pyridyl | V | CH$_2$CH$_2$CH$_3$ | CH | O |
| 11.67 | 4-pyrimidyl | V | CH$_2$CH$_2$CH$_3$ | CH | O |
| 11.68 | 2-thienyl | V | CH$_2$CH$_2$CH$_3$ | CH | O |
| 11.69 | 3-thienyl | V | CH$_2$CH$_2$CH$_3$ | CH | O |
| 11.70 | 2-napthyl | V | CH$_2$CH$_2$CH$_3$ | CH | O |

Further typical compounds described by the present invention are described in the following tables.

Table 12:
Compounds 12.1 to 12.47 are Compounds of Table 11 of Formula V, VI, VII where Z is Ar.

Table 13:
Compounds 13.1 to 13.47 are Compounds of Table 11 of Formula V, VI, VII where Z is CH$_2$Ar.

Table 14:
Compounds 14.1 to 14.47 are Compounds of Table 11 of Formula V, VI, VII where Z is CH$_2$CF$_3$.

Table 15:
Compounds 15.1 to 15.47 are Compounds of Table 12 of Formula V, VI, VII where V=O and A is N.

Table 16:
Compounds 16.1 to 16.47 are Compounds of Table 12 of Formula V, VI, VII where V=NH and A is N.

Table 17:
Compounds 17.1 to 17.47 are Compounds of Table 13 of Formula V, VI, VII where V=O and A is N Table 18:
Compounds 18.1 to 18.47 are Compounds of Table 13 of Formula V, VI, VII where V=NH and A is N.

Table 19:
Compounds 19.1 to 19.47 are Compounds of Table 14 of Formula V, VI, VII where V=O and A is N.

Table 20:
Compounds 20.1 to 20.47 are Compounds of Table 14 of Formula V, VI, VII where V=NH and A is N.

Typical compounds encompassed by the present invention of Formula I include those compounds presented in Table 21 of Formula VIII, IX and X where X=H, R$_1$=H, U and W are N and n=0 and m=1.

TABLE 21

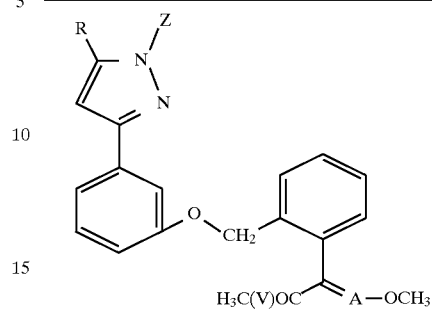

(VIII)

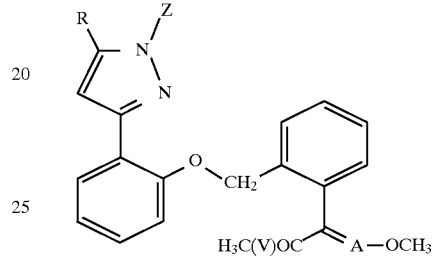

(IX)

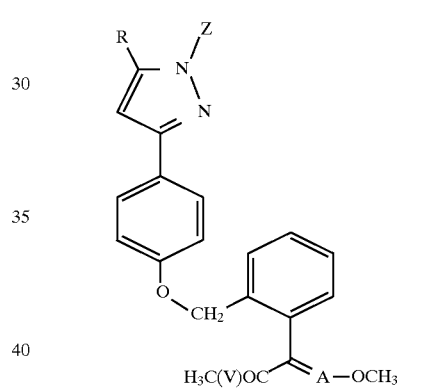

(X)

| Cmpd# | R | Formula | Z | A | V |
|---|---|---|---|---|---|
| 21.01 | Ar | VIII | CH$_3$ | CH | O |
| 21.02 | Ar | IX | CH$_3$ | CH | O |
| 21.03 | Ar | X | CH$_3$ | CH | O |
| 21.04 | 4-Cl(Ar) | VIII | CH$_3$ | CH | O |
| 21.05 | 4-Cl(Ar) | IX | CH$_3$ | CH | O |
| 21.06 | 4-Cl(Ar) | X | CH$_3$ | CH | O |
| 21.07 | 4-F(Ar) | VIII | CH$_3$ | CH | O |
| 21.08 | 4-F(Ar) | IX | CH$_3$ | CH | O |
| 21.09 | 4-F(Ar) | X | CH$_3$ | CH | O |
| 21.10 | 2-CH$_3$(Ar) | VIII | CH$_3$ | CH | O |
| 21.11 | 2-CH$_3$(Ar) | IX | CH$_3$ | CH | O |
| 21.12 | 2-CH$_3$(Ar) | X | CH$_3$ | CH | O |
| 21.13 | 4-CH$_3$(Ar) | VIII | CH$_3$ | CH | O |
| 21.14 | 4-CH$_3$(Ar) | IX | CH$_3$ | CH | O |
| 21.15 | 4-CH$_3$(Ar) | X | CH$_3$ | CH | O |
| 21.16 | 4-CF$_3$(Ar) | VIII | CH$_3$ | CH | O |
| 21.17 | 2,4-Cl(Ar) | VIII | CH$_3$ | CH | O |
| 21.18 | CH$_3$ | VIII | CH$_3$ | CH | O |
| 21.19 | CH$_2$CH$_3$ | VIII | CH$_3$ | CH | O |
| 21.20 | CH$_2$CH$_2$CH$_3$ | VIII | CH$_3$ | CH | O |
| 21.21 | CH(CH$_3$)$_2$ | VIII | CH$_3$ | CH | O |
| 21.22 | CH$_2$(CH$_2$)$_3$CH$_3$ | VIII | CH$_3$ | CH | O |
| 21.23 | CH$_2$(CH$_2$)$_4$CH$_3$ | VIII | CH$_3$ | CH | O |
| 21.24 | CH$_2$CH(CH$_3$)$_2$ | VIII | CH$_3$ | CH | O |
| 21.25 | CH(CH$_3$)CH$_2$CH$_3$ | VIII | CH$_3$ | CH | O |
| 21.26 | C(CH$_3$)$_3$ | VIII | CH$_3$ | CH | O |
| 21.27 | CH$_2$C(CH$_3$)$_3$ | VIII | CH$_3$ | CH | O |
| 21.28 | CH(CH$_3$)CH$_2$CH$_2$CH$_3$ | VIII | CH$_3$ | CH | O |

TABLE 21-continued

| | | | | | |
|---|---|---|---|---|---|
| 21.29 | C(CH$_3$)$_2$CH$_2$CH$_3$ | VIII | CH$_3$ | CH | O |
| 21.30 | CF$_3$ | VIII | CH$_3$ | CH | O |
| 21.31 | CF$_2$CF$_3$ | VIII | CH$_3$ | CH | O |
| 21.32 | CH$_2$CF$_3$ | VIII | CH$_3$ | CH | O |
| 21.33 | CH=CH$_2$ | VIII | CH$_3$ | CH | O |
| 21.34 | cyclopropyl | VIII | CH$_3$ | CH | O |
| 21.35 | cyclopentyl | VIII | CH$_3$ | CH | O |
| 21.36 | cyclohexyl | VIII | CH$_3$ | CH | O |
| 21.37 | CH$_2$OCH$_3$ | VIII | CH$_3$ | CH | O |
| 21.38 | CH$_2$OCH$_2$CH$_3$ | VIII | CH$_3$ | CH | O |
| 21.39 | CH$_2$CH$_2$OCOAr | VIII | CH$_3$ | CH | O |
| 21.40 | CH$_2$OCH$_2$Ar | VIII | CH$_3$ | CH | O |
| 21.41 | 2-pyridyl | VIII | CH$_3$ | CH | O |
| 21.42 | 3-pyridyl | VIII | CH$_3$ | CH | O |
| 21.43 | 2-pyrimidyl | VIII | CH$_3$ | CH | O |
| 21.44 | 4-pyrimidyl | VIII | CH$_3$ | CH | O |
| 21.45 | 2-thienyl | VIII | CH$_3$ | CH | O |
| 21.46 | 3-thienyl | VIII | CH$_3$ | CH | O |
| 21.47 | 2-napthyl | VIII | CH$_3$ | CH | O |
| 21.48 | Ar | VIII | Ar | CH | O |
| 21.49 | 4-Cl(Ar) | VIII | Ar | CH | O |
| 21.50 | CH$_3$ | VIII | Ar | CH | O |
| 21.51 | CH$_2$CH$_3$ | VIII | Ar | CH | O |
| 21.52 | CH$_2$CH$_2$CH$_3$ | VIII | Ar | CH | O |
| 21.53 | CH(CH$_3$)$_2$ | VIII | Ar | CH | O |
| 21.54 | CH$_2$(CH$_2$)$_3$CH$_3$ | VIII | Ar | CH | O |
| 21.55 | CH$_2$CH(CH$_3$)$_2$ | VIII | Ar | CH | O |
| 21.56 | C(CH$_3$)$_3$ | VIII | Ar | CH | O |
| 21.57 | Ar | VIII | CH$_2$Ar | CH | O |
| 21.58 | 4-Cl(Ar) | VIII | CH$_2$Ar | CH | O |
| 21.59 | CH$_3$ | VIII | CH$_2$Ar | CH | O |
| 21.60 | CH$_2$CH$_2$CH$_3$ | VIII | CH$_2$Ar | CH | O |
| 21.61 | CH(CH$_3$)$_2$ | VIII | CH$_2$Ar | CH | O |
| 21.62 | CH$_2$(CH$_2$)$_3$CH$_3$ | VIII | CH$_2$Ar | CH | O |
| 21.63 | CH$_2$CH(CH$_3$)$_2$ | VIII | CH$_2$Ar | CH | O |
| 21.64 | C(CH$_3$)$_3$ | VIII | CH$_2$Ar | CH | O |
| 21.65 | Ar | VIII | CF$_2$CF$_3$ | CH | O |
| 21.66 | 4-Cl(Ar) | VIII | CF$_2$CF$_3$ | CH | O |
| 21.67 | CH$_3$ | VIII | CF$_2$CF$_3$ | CH | O |
| 21.68 | CH$_2$CH$_2$CH$_3$ | VIII | CF$_2$CF$_3$ | CH | O |
| 21.69 | C(CH$_3$)$_3$ | VIII | CF$_2$CF$_3$ | CH | O |
| 21.70 | 2-thienyl | VIII | CF$_2$CF$_3$ | CH | O |

Further typical compounds described by the present invention are described in the following tables.

Table 22

Compounds 22.1 to 22.70 are Compounds of Table 19 of Formula VIII, IX, X where V=O and A is N.

Table 23:

Compounds 23.1 to 23.70 are Compounds of Table 19 of Formula VIII, IX, X where V=NH and A is N.

Typical compounds encompassed by the present invention of Formula I include those compounds presented in Table 24. of Formula XI, XII, XIII where X=H, R$_1$=H, U and W are N and n=1 and m=0.

TABLE 24

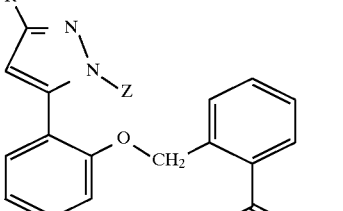

(XI)

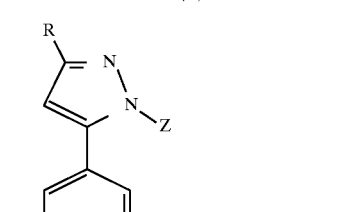

(XII)

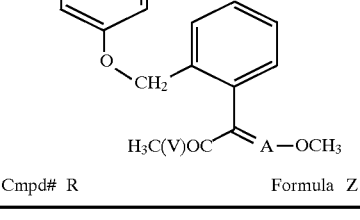

(XIII)

| Cmpd# | R | Formula | Z | A | V |
|---|---|---|---|---|---|
| 24.01 | Ar | XI | CH$_3$ | CH | O |
| 24.02 | Ar | XII | CH$_3$ | CH | O |
| 24.03 | Ar | XIII | CH$_3$ | CH | O |
| 24.04 | 4-Cl(Ar) | XI | CH$_3$ | CH | O |
| 24.05 | 4-Cl(Ar) | XII | CH$_3$ | CH | O |
| 24.06 | 4-Cl(Ar) | XIII | CH$_3$ | CH | O |
| 24.07 | 4-F(Ar) | XI | CH$_3$ | CH | O |
| 24.08 | 4-F(Ar) | XII | CH$_3$ | CH | O |
| 24.09 | 4-F(Ar) | XIII | CH$_3$ | CH | O |
| 24.10 | 2-CH$_3$(Ar) | XI | CH$_3$ | CH | O |
| 24.11 | 2-CH$_3$(Ar) | XII | CH$_3$ | CH | O |
| 24.12 | 2-CH$_3$(Ar) | XIII | CH$_3$ | CH | O |
| 24.13 | 4-CH$_3$(Ar) | XI | CH$_3$ | CH | O |
| 24.14 | 4-CH$_3$(Ar) | XII | CH$_3$ | CH | O |
| 24.15 | 4-CH$_3$(Ar) | XIII | CH$_3$ | CH | O |
| 24.16 | 4-CF$_3$(Ar) | XIII | CH$_3$ | CH | O |
| 24.17 | 2,4-Cl(Ar) | XIII | CH$_3$ | CH | O |
| 24.18 | CH$_3$ | XIII | CH$_3$ | CH | O |
| 24.19 | CH$_2$CH$_3$ | XIII | CH$_3$ | CH | O |
| 24.20 | CH$_2$CH$_2$CH$_3$ | XIII | CH$_3$ | CH | O |
| 24.21 | CH(CH$_3$)$_2$ | XIII | CH$_3$ | CH | O |
| 24.22 | CH$_2$(CH$_2$)$_3$CH$_3$ | XIII | CH$_3$ | CH | O |
| 24.23 | CH$_2$(CH$_2$)$_4$CH$_3$ | XIII | CH$_3$ | CH | O |
| 24.24 | CH$_2$CH(CH$_3$)$_2$ | XIII | CH$_3$ | CH | O |
| 24.25 | CH(CH$_3$)CH$_2$CH$_3$ | XIII | CH$_3$ | CH | O |
| 24.26 | C(CH$_3$)$_3$ | XIII | CH$_3$ | CH | O |
| 24.27 | CH$_2$C(CH$_3$)$_3$ | XIII | CH$_3$ | CH | O |
| 24.28 | CH(CH$_3$)CH$_2$CH$_2$CH$_3$ | XIII | CH$_3$ | CH | O |
| 24.29 | C(CH$_3$)$_2$CH$_2$CH$_3$ | XIII | CH$_3$ | CH | O |
| 24.30 | CF$_3$ | XIII | CH$_3$ | CH | O |
| 24.31 | CF$_2$CF$_3$ | XIII | CH$_3$ | CH | O |
| 24.32 | CH$_2$CF$_3$ | XIII | CH$_3$ | CH | O |
| 24.33 | CH=CH$_2$ | XIII | CH$_3$ | CH | O |
| 24.34 | cyclopropyl | XIII | CH$_3$ | CH | O |
| 24.35 | cyclopentyl | XIII | CH$_3$ | CH | O |
| 24.36 | cyclohexyl | XIII | CH$_3$ | CH | O |
| 24.37 | CH$_2$OCH$_3$ | XIII | CH$_3$ | CH | O |
| 24.38 | CH$_2$OCH$_2$CH$_3$ | XIII | CH$_3$ | CH | O |
| 24.39 | CH$_2$CH$_2$OCOAr | XIII | CH$_3$ | CH | O |
| 24.40 | CH$_2$OCH$_2$Ar | XIII | CH$_3$ | CH | O |
| 24.41 | 2-pyridyl | XIII | CH$_3$ | CH | O |
| 24.42 | 3-pyridyl | XIII | CH$_3$ | CH | O |
| 24.43 | 2-pyrimidyl | XIII | CH$_3$ | CH | O |
| 24.44 | 4-pyrimidyl | XIII | CH$_3$ | CH | O |
| 24.45 | 2-thienyl | XIII | CH$_3$ | CH | O |
| 24.46 | 3-thienyl | XIII | CH$_3$ | CH | O |

TABLE 24-continued

| | | | | | |
|---|---|---|---|---|---|
| 24.47 | 2-napthyl | XIII | $CH_3$ | CH | O |
| 24.48 | Ar | XIII | Ar | CH | O |
| 24.49 | 4-Cl(Ar) | XIII | Ar | CH | O |
| 24.50 | $CH_3$ | XIII | Ar | CH | O |
| 24.51 | $CH_2CH_3$ | XIII | Ar | CH | O |
| 24.52 | $CH_2CH_2CH_3$ | XIII | Ar | CH | O |
| 24.53 | $CH(CH_3)_2$ | XIII | Ar | CH | O |
| 24.54 | $CH_2(CH_2)_3CH_3$ | XIII | Ar | CH | O |
| 24.55 | $CH_2CH(CH_3)_2$ | XIII | Ar | CH | O |
| 24.56 | $C(CH_3)_3$ | XIII | Ar | CH | O |
| 24.57 | Ar | XIII | $CH_2Ar$ | CH | O |
| 24.58 | 4-Cl(Ar) | XIII | $CH_2Ar$ | CH | O |
| 24.59 | $CH_3$ | XIII | $CH_2Ar$ | CH | O |
| 24.60 | $CH_2CH_2CH_3$ | XIII | $CH_2Ar$ | CH | O |
| 24.61 | $CH(CH_3)_2$ | XIII | $CH_2Ar$ | CH | O |
| 24.62 | $CH_2(CH_2)_3CH_3$ | XIII | $CH_2Ar$ | CH | O |
| 24.63 | $CH_2CH(CH_3)_2$ | XIII | $CH_2Ar$ | CH | O |
| 24.64 | $C(CH_3)_3$ | XIII | $CH_2Ar$ | CH | O |
| 24.65 | Ar | XIII | $CF_2CF_3$ | CH | O |
| 24.66 | 4-Cl(Ar) | XIII | $CF_2CF_3$ | CH | O |
| 24.67 | $CH_3$ | XIII | $CF_2CF_3$ | CH | O |
| 24.68 | $CH_2CH_2CH_3$ | XIII | $CF_2CF_3$ | CH | O |
| 24.69 | $C(CH_3)_3$ | XIII | $CF_2CF_3$ | CH | O |
| 24.70 | 2-thienyl | XIII | $CF_2CF_3$ | CH | O |

Further typical compounds described by the present invention are described in the following tables.

Table 25:

Compounds 25.01 to 25.70 are Compounds of Table 24 of Formula XI, XII, XIII where V=O and A is N.

Table 26:

Compounds 26.01 to 26.70 are Compounds of Table 24 of Formula XI, XII, XIII where V=NH and A is N.

Typical compounds encompassed by the present invention of Formula I include those compounds presented in Table 27. of Formula XIV, XV, XVI where X=H, $R_1$=H, U is O, W is N and n and m are 0.

TABLE 27

(XIV)

(XV)

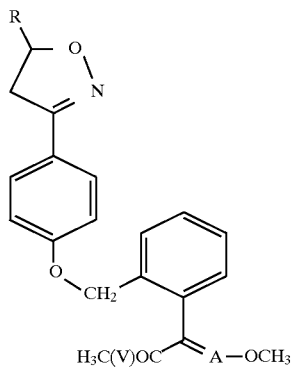

(XVI)

| Cmpd# | R | Formula | A | V |
|---|---|---|---|---|
| 27.01 | Ar | XIV | CH | O |
| 27.02 | Ar | XV | CH | O |
| 27.03 | Ar | XVI | CH | O |
| 27.04 | 4-Cl(Ar) | XIV | CH | O |
| 27.05 | 4-Cl(Ar) | XV | CH | O |
| 27.06 | 4-Cl(Ar) | XVI | CH | O |
| 27.07 | 4-F(Ar) | XIV | CH | O |
| 27.08 | 4-F(Ar) | XV | CH | O |
| 27.09 | 4-F(Ar) | XVI | CH | O |
| 27.10 | 2-$CH_3$(Ar) | XIV | CH | O |
| 27.11 | 2-$CH_3$(Ar) | XV | CH | O |
| 27.12 | 2-$CH_3$(Ar) | XVI | CH | O |
| 27.13 | 4-$CH_3$(Ar) | XIV | CH | O |
| 27.14 | 4-$CH_3$(Ar) | XV | CH | O |
| 27.15 | 4-$CH_3$(Ar) | XVI | CH | O |
| 27.16 | 4-$CF_3$(Ar) | XIV | CH | O |
| 27.17 | 2,4-Cl(Ar) | XIV | CH | O |
| 27.18 | $CH_3$ | XIV | CH | O |
| 27.19 | $CH_2CH_3$ | XIV | CH | O |
| 27.20 | $CH_2CH_2CH_3$ | XIV | CH | O |
| 27.21 | $CH(CH_3)_2$ | XIV | CH | O |
| 27.22 | $CH_2(CH_2)_3CH_3$ | XIV | CH | O |
| 27.23 | $CH_2(CH_2)_4CH_3$ | XIV | CH | O |
| 27.24 | $CH_2CH(CH_3)_2$ | XIV | CH | O |
| 27.25 | $CH(CH_3)CH_2CH_3$ | XIV | CH | O |
| 27.26 | $C(CH_3)_3$ | XIV | CH | O |
| 27.27 | $CH_2C(CH_3)_3$ | XIV | CH | O |
| 27.28 | $CH(CH_3)CH_2CH_2CH_3$ | XIV | CH | O |
| 27.29 | $C(CH_3)_2CH_2CH_3$ | XIV | CH | O |
| 27.30 | $CF_3$ | XIV | CH | O |
| 27.31 | $CF_2CF_3$ | XIV | CH | O |
| 27.32 | $CH_2CF_3$ | XIV | CH | O |
| 27.33 | $CH=CH_2$ | XIV | CH | O |
| 27.34 | cyclopropyl | XIV | CH | O |
| 27.35 | cyclopentyl | XIV | CH | O |
| 27.36 | cyclohexyl | XIV | CH | O |
| 27.37 | $CH_2OCH_3$ | XIV | CH | O |
| 27.38 | $CH_2OCH_2CH_3$ | XIV | CH | O |
| 27.39 | $CH_2CH_2OCOAr$ | XIV | CH | O |
| 27.40 | $CH_2OCH_2Ar$ | XIV | CH | O |
| 27.41 | 2-pyridyl | XIV | CH | O |
| 27.42 | 3-pyridyl | XIV | CH | O |
| 27.43 | 2-pyrimidyl | XIV | CH | O |
| 27.44 | 4-pyrimidyl | XIV | CH | O |
| 27.45 | 2-thienyl | XIV | CH | O |
| 27.46 | 3-thienyl | XIV | CH | O |
| 27.47 | 2-napthyl | XIV | CH | O |
| 27.48 | Ar | XIV | N | O |
| 27.49 | 4-Cl(Ar) | XIV | N | O |
| 27.50 | $CH_3$ | XIV | N | O |
| 27.51 | $CH_2CH_3$ | XIV | N | O |
| 27.52 | $CH_2CH_2CH_3$ | XIV | N | O |
| 27.53 | $CH(CH_3)_2$ | XIV | N | O |
| 27.54 | $CH_2(CH_2)_3CH_3$ | XIV | N | O |
| 27.55 | $CH_2CH(CH_3)_2$ | XIV | N | O |
| 27.56 | $C(CH_3)_3$ | XIV | N | O |
| 27.57 | Ar | XIV | N | NH |
| 27.58 | 4-Cl(Ar) | XIV | N | NH |
| 27.59 | $CH_3$ | XIV | N | NH |

TABLE 27-continued

| | | | | |
|---|---|---|---|---|
| 27.60 | $CH_2CH_2CH_3$ | XIV | N | NH |
| 27.61 | $CH(CH_3)_2$ | XIV | N | NH |
| 27.62 | $CH_2(CH_2)_3CH_3$ | XIV | N | NH |
| 27.63 | $CH_2CH(CH_3)_2$ | XIV | N | NH |
| 27.64 | $C(CH_3)_3$ | XIV | N | NH |
| 27.65 | 2-thienyl | XIV | N | NH |
| 27.66 | 3-thienyl | XIV | N | NH |
| 27.67 | 2-pyridyl | XIV | N | NH |
| 27.68 | 3-pyridyl | XIV | N | NH |
| 27.69 | 5-pyrimidinyl | XIV | N | NH |
| 27.70 | 2-napthyl | XIV | N | NH |

Typical compounds encompassed by the present invention of Formula I include those compounds presented in Table 28. of Formula XVII, XVIII, XIX where X=H, $R_1$=H, U is N, W is O and n and m are 0.

TABLE 28

(XVII) — structure with R group on isoxazoline linked via phenyl-O-$CH_2$-phenyl to $H_3C(V)OC$—A—$OCH_3$ (XVIII) — analogous structure (XIX) — analogous structure (para-substituted phenyl)

| Cmpd# | R | Formula | A | V |
|---|---|---|---|---|
| 28.01 | Ar | XVII | CH | O |
| 28.02 | Ar | XVIII | CH | O |
| 28.03 | Ar | XIX | CH | O |
| 28.04 | 4-Cl(Ar) | XVII | CH | O |
| 28.05 | 4-Cl(Ar) | XVIII | CH | O |
| 28.06 | 4-Cl(Ar) | XIX | CH | O |
| 28.07 | 4-FAr) | XVII | CH | O |
| 28.08 | 4-F(Ar) | XVIII | CH | O |
| 28.09 | 4-F(Ar) | XIX | CH | O |
| 28.10 | 2-$CH_3$(Ar) | XVII | CH | O |
| 28.11 | 2-$CH_3$(Ar) | XVIII | CH | O |
| 28.12 | 2-$CH_3$(Ar) | XIX | CH | O |
| 28.13 | 4-$CH_3$(Ar) | XVII | CH | O |
| 28.14 | 4-$CH_3$(Ar) | XVIII | CH | O |
| 28.15 | 4-$CH_3$(Ar) | XIX | CH | O |
| 28.16 | 4-$CF_3$(Ar) | XIX | CH | O |
| 28.17 | 2,4-Cl(Ar) | XIX | CH | O |
| 28.18 | $CH_3$ | XIX | CH | O |
| 28.19 | $CH_2CH_3$ | XIX | CH | O |
| 28.20 | $CH_2CH_2CH_3$ | XIX | CH | O |
| 28.21 | $CH(CH_3)_2$ | XIX | CH | O |
| 28.22 | $CH_2(CH_2)_3CH_3$ | XIX | CH | O |
| 28.23 | $CH_2(CH_2)_4CH_3$ | XIX | CH | O |
| 28.24 | $CH_2CH(CH_3)_2$ | XIX | CH | O |
| 28.25 | $CH(CH_3)CH_2CH_3$ | XIX | CH | O |
| 28.26 | $C(CH_3)_3$ | XIX | CH | O |
| 28.27 | $CH_2C(CH_3)_3$ | XIX | CH | O |
| 28.28 | $CH(CH_3)CH_2CH_2CH_3$ | XIX | CH | O |
| 28.29 | $C(CH_3)_2CH_2CH_3$ | XIX | CH | O |
| 28.30 | $CF_3$ | XIX | CH | O |
| 28.31 | $CF_2CF_3$ | XIX | CH | O |
| 28.32 | $CH_2CF_3$ | XIX | CH | O |
| 28.33 | $CH=CH_2$ | XIX | CH | O |
| 28.34 | cyclopropyl | XIX | CH | O |
| 28.35 | cyclopentyl | XIX | CH | O |
| 28.36 | cyclohexyl | XIX | CH | O |
| 28.37 | $CH_2OCH_3$ | XIX | CH | O |
| 28.38 | $CH_2OCH_2CH_3$ | XIX | CH | O |
| 28.39 | $CH_2CH_2OCOAr$ | XIX | CH | O |
| 28.40 | $CH_2OCH_2Ar$ | XIX | CH | O |
| 28.41 | 2-pyridyl | XIX | CH | O |
| 28.42 | 3-pyridyl | XIX | CH | O |
| 28.43 | 2-pyrimidyl | XIX | CH | O |
| 28.44 | 4-pyrimidyl | XIX | CH | O |
| 28.45 | 2-thienyl | XIX | CH | O |
| 28.46 | 3-thienyl | XIX | CH | O |
| 28.47 | 2-napthyl | XIX | CH | O |
| 28.48 | Ar | XIX | N | O |
| 28.49 | 4-Cl(Ar) | XIX | N | O |
| 28.50 | $CH_3$ | XIX | N | O |
| 28.51 | $CH_2CH_3$ | XIX | N | O |
| 28.52 | $CH_2CH_2CH_3$ | XIX | N | O |
| 28.53 | $CH(CH_3)_2$ | XIX | N | O |
| 28.54 | $CH_2(CH_2)_3CH_3$ | XIX | N | O |
| 28.55 | $CH_2CH(CH_3)_2$ | XIX | N | O |
| 28.56 | $C(CH_3)_3$ | XIX | N | O |
| 28.57 | Ar | XIX | N | NH |
| 28.58 | 4-Cl(Ar) | XIX | N | NH |
| 28.59 | $CH_3$ | XIX | N | NH |
| 28.60 | $CH_2CH_2CH_3$ | XIX | N | NH |
| 28.61 | $CH(CH_3)_2$ | XIX | N | NH |
| 28.62 | $CH_2(CH_2)_3CH_3$ | XIX | N | NH |
| 28.63 | $CH_2CH(CH_3)_2$ | XIX | N | NH |
| 28.64 | $C(CH_3)_3$ | XIX | N | NH |
| 28.65 | 2-thienyl | XIX | N | NH |
| 28.66 | 3-thienyl | XIX | N | NH |
| 28.67 | 2-pyridyl | XIX | N | NH |
| 28.68 | 3-pyridyl | XIX | N | NH |
| 28.69 | 5-pyrimidinyl | XIX | N | NH |
| 28.70 | 2-napthyl | XIX | N | NH |

Typical compounds encompassed by the present invention of Formula I include those compounds presented in Table 29. of Formula XX, XXI, XXII where X=H, $R_1$=H, U is O, W is N and n and m are 0.

TABLE 29

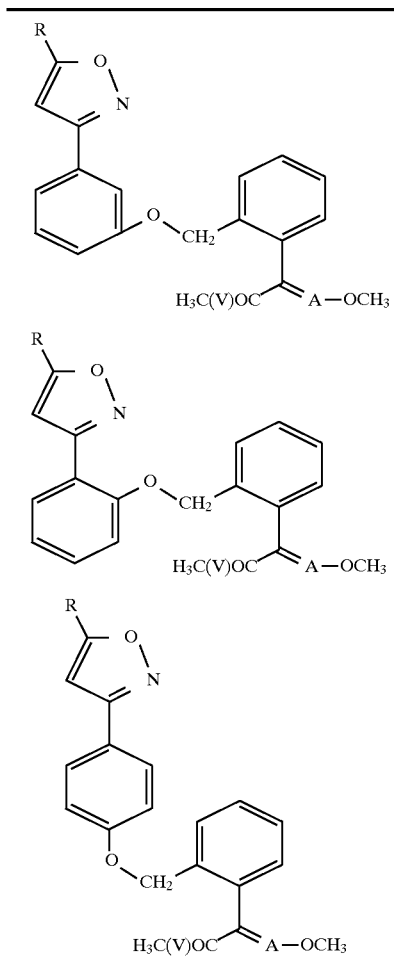

| Cmpd# | R | Formula | A | V |
|---|---|---|---|---|
| 29.01 | Ar | XX | CH | O |
| 29.02 | Ar | XXI | CH | O |
| 29.03 | Ar | XXII | CH | O |
| 29.04 | 4-Cl(Ar) | XX | CH | O |
| 29.05 | 4-Cl(Ar) | XXI | CH | O |
| 29.06 | 4-Cl(Ar) | XXII | CH | O |
| 29.07 | 4-F(Ar) | XX | CH | O |
| 29.08 | 4-F(Ar) | XXI | CH | O |
| 29.09 | 4-F(Ar) | XXII | CH | O |
| 29.10 | 2-CH$_3$(Ar) | XX | CH | O |
| 29.11 | 2-CH$_3$(Ar) | XXI | CH | O |
| 29.12 | 2-CH$_3$(Ar) | XXII | CH | O |
| 29.13 | 4-CH$_3$(Ar) | XX | CH | O |
| 29.14 | 4-CH$_3$(Ar) | XXI | CH | O |
| 29.15 | 4-CH$_3$(Ar) | XXII | CH | O |
| 29.16 | 4-CF$_3$(Ar) | XX | CH | O |
| 29.17 | 2,4-Cl(Ar) | XX | CH | O |
| 29.18 | CH$_3$ | XX | CH | O |
| 29.19 | CH$_2$CH$_3$ | XX | CH | O |
| 29.20 | CH$_2$CH$_2$CH$_3$ | XX | CH | O |
| 29.21 | CH(CH$_3$)$_2$ | XX | CH | O |
| 29.22 | CH$_2$(CH$_2$)$_3$CH$_3$ | XX | CH | O |
| 29.23 | CH$_2$(CH$_2$)$_4$CH$_3$ | XX | CH | O |
| 29.24 | CH$_2$CH(CH$_3$)$_2$ | XX | CH | O |
| 29.25 | CH(CH$_3$)CH$_2$CH$_3$ | XX | CH | O |
| 29.26 | C(CH$_3$)$_3$ | XX | CH | O |
| 29.27 | CH$_2$C(CH$_3$)$_3$ | XX | CH | O |
| 29.28 | CH(CH$_3$)CH$_2$CH$_2$CH$_3$ | XX | CH | O |
| 29.29 | C(CH$_3$)$_2$CH$_2$CH$_3$ | XX | CH | O |
| 29.30 | CF$_3$ | XX | CH | O |
| 29.31 | CF$_2$CF$_3$ | XX | CH | O |
| 29.32 | CH$_2$CF$_3$ | XX | CH | O |
| 29.33 | CH=CH$_2$ | XX | CH | O |
| 29.34 | cyclopropyl | XX | CH | O |
| 29.35 | cyclopentyl | XX | CH | O |
| 29.36 | cyclohexyl | XX | CH | O |
| 29.37 | CH$_2$OCH$_3$ | XX | CH | O |
| 29.38 | CH$_2$OCH$_2$CH$_3$ | XX | CH | O |
| 29.39 | CH$_2$CH$_2$OCOAr | XX | CH | O |
| 29.40 | CH$_2$OCH$_2$Ar | XX | CH | O |
| 29.41 | 2-pyridyl | XX | CH | O |
| 29.42 | 3-pyridyl | XX | CH | O |
| 29.43 | 2-pyrimidyl | XX | CH | O |
| 29.44 | 4-pyrimidyl | XX | CH | O |
| 29.45 | 2-thienyl | XX | CH | O |
| 29.46 | 3-thienyl | XX | CH | O |
| 29.47 | 2-napthyl | XX | CH | O |
| 29.48 | Ar | XX | N | O |
| 29.49 | 4-Cl(Ar) | XX | N | O |
| 29.50 | CH$_3$ | XX | N | O |
| 29.51 | CH$_2$CH$_3$ | XX | N | O |
| 29.52 | CH$_2$CH$_2$CH$_3$ | XX | N | O |
| 29.53 | CH(CH$_3$)$_2$ | XX | N | O |
| 29.54 | CH$_2$(CH$_2$)$_3$CH$_3$ | XX | N | O |
| 29.55 | CH$_2$CH(CH$_3$)$_2$ | XX | N | O |
| 29.56 | C(CH$_3$)$_3$ | XX | N | O |
| 29.57 | Ar | XX | N | NH |
| 29.58 | 4-Cl(Ar) | XX | N | NH |
| 29.59 | CH$_3$ | XX | N | NH |
| 29.60 | CH$_2$CH$_2$CH$_3$ | XX | N | NH |
| 29.61 | CH(CH$_3$)$_2$ | XX | N | NH |
| 29.62 | CH$_2$(CH$_2$)$_3$CH$_3$ | XX | N | NH |
| 29.63 | CH$_2$CH(CH$_3$)$_2$ | XX | N | NH |
| 29.64 | C(CH$_3$)$_3$ | XX | N | NH |
| 29.65 | 2-thienyl | XX | N | NH |
| 29.66 | 3-thienyl | XX | N | NH |
| 29.67 | 2-pyridyl | XX | N | NH |
| 29.68 | 3-pyridyl | XX | N | NH |
| 29.69 | 5-pyrimidinyl | XX | N | NH |
| 29.70 | 2-napthyl | XX | N | NH |

Typical compounds encompassed by the present invention of Formula I include those compounds presented in Table 30. of Formula XXIII, XXIV, XXV where X=H, R$_1$=H, U is N, W is O and n and m are 0.

TABLE 30

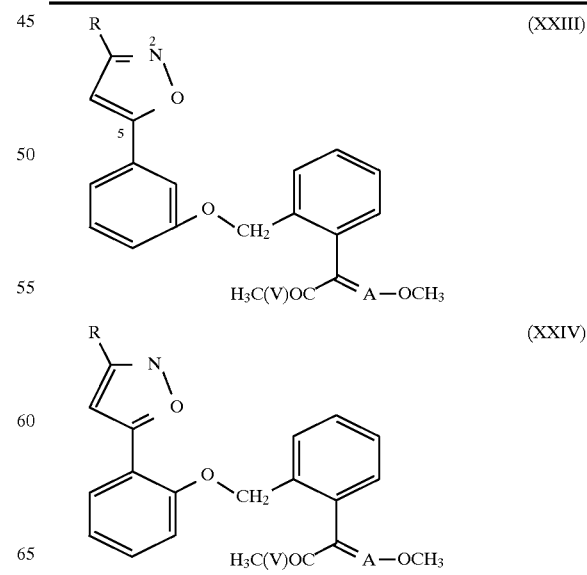

TABLE 30-continued (XXV structure with R group on isoxazole, linked via phenyl-O-CH2-phenyl to H3C(V)OC...A—OCH3)

| Cmpd# | R | Formula | A | V |
|---|---|---|---|---|
| 30.01 | Ar | XXIII | CH | O |
| 30.02 | Ar | XXIV | CH | O |
| 30.03 | Ar | XXV | CH | O |
| 30.04 | 4-Cl(Ar) | XXIII | CH | O |
| 30.05 | 4-Cl(Ar) | XXIV | CH | O |
| 30.06 | 4-Cl(Ar) | XXV | CH | O |
| 30.07 | 4-F(Ar) | XXIII | CH | O |
| 30.08 | 4-F(Ar) | XXIV | CH | O |
| 30.09 | 4-F(Ar) | XXV | CH | O |
| 30.10 | 2-$CH_3$(Ar) | XXIII | CH | O |
| 30.11 | 2-$CH_3$(Ar) | XXIV | CH | O |
| 30.12 | 2-$CH_3$(Ar) | XXV | CH | O |
| 30.13 | 4-$CH_3$(Ar) | XXIII | CH | O |
| 30.14 | 4-$CH_3$(Ar) | XXIV | CH | O |
| 30.15 | 4-$CH_3$(Ar) | XXV | CH | O |
| 30.16 | 4-$CF_3$(Ar) | XXIII | CH | O |
| 30.17 | 2,4-Cl(Ar) | XXIII | CH | O |
| 30.18 | $CH_3$ | XXIII | CH | O |
| 30.19 | $CH_2CH_3$ | XXIII | CH | O |
| 30.20 | $CH_2CH_2CH_3$ | XXIII | CH | O |
| 30.21 | $CH(CH_3)_2$ | XXIII | CH | O |
| 30.22 | $CH_2(CH_2)_3CH_3$ | XXIII | CH | O |
| 30.23 | $CH_2(CH_2)_4CH_3$ | XXIII | CH | O |
| 30.24 | $CH_2CH(CH_3)_2$ | XXIII | CH | O |
| 30.25 | $CH(CH_3)CH_2CH_3$ | XXIII | CH | O |
| 30.26 | $C(CH_3)_3$ | XXIII | CH | O |
| 30.27 | $CH_2C(CH_3)_3$ | XXIII | CH | O |
| 30.28 | $CH(CH_3)CH_2CH_2CH_3$ | XXIII | CH | O |
| 30.29 | $C(CH_3)_2CH_2CH_3$ | XXIII | CH | O |
| 30.30 | $CF_3$ | XXIII | CH | O |
| 30.31 | $CF_2CF_3$ | XXIII | CH | O |
| 30.32 | $CH_2CF_3$ | XXIII | CH | O |
| 30.33 | $CH=CH_2$ | XXIII | CH | O |
| 30.34 | cyclopropyl | XXIII | CH | O |
| 30.35 | cyclopentyl | XXIII | CH | O |
| 30.36 | cyclohexyl | XXIII | CH | O |
| 30.37 | $CH_2OCH_3$ | XXIII | CH | O |
| 30.38 | $CH_2OCH_2CH_3$ | XXIII | CH | O |
| 30.39 | $CH_2CH_2OCOAr$ | XXIII | CH | O |
| 30.40 | $CH_2OCH_2Ar$ | XXIII | CH | O |
| 30.41 | 2-pyridyl | XXIII | CH | O |
| 30.42 | 3-pyridyl | XXIII | CH | O |
| 30.43 | 2-pyrimidyl | XXIII | CH | O |
| 30.44 | 4-pyrimidyl | XXIII | CH | O |
| 30.45 | 2-thienyl | XXIII | CH | O |
| 30.46 | 3-thienyl | XXIII | CH | O |
| 30.47 | 2-napthyl | XXIII | CH | O |
| 30.48 | Ar | XXIII | N | O |
| 30.49 | 4-Cl(Ar) | XXIII | N | O |
| 30.50 | $CH_3$ | XXIII | N | O |
| 30.51 | $CH_2CH_3$ | XXIII | N | O |
| 30.52 | $CH_2CH_2CH_3$ | XXIII | N | O |
| 30.53 | $CH(CH_3)_2$ | XXIII | N | O |
| 30.54 | $CH_2(CH_2)_3CH_3$ | XXIII | N | O |
| 30.55 | $CH_2CH(CH_3)_2$ | XXIII | N | O |
| 30.56 | $C(CH_3)_3$ | XXIII | N | O |
| 30.57 | (Ar) | XXIII | N | NH |
| 30.58 | 4-Cl(Ar) | XXIII | N | NH |
| 30.59 | $CH_3$ | XXIII | N | NH |
| 30.60 | $CH_2CH_2CH_3$ | XXIII | N | NH |
| 30.61 | $CH(CH_3)_2$ | XXIII | N | NH |
| 30.62 | $CH_2(CH_2)_3CH_3$ | XXIII | N | NH |
| 30.63 | $CH_2CH(CH_3)_2$ | XXIII | N | NH |
| 30.64 | $C(CH_3)_3$ | XXIII | N | NH |
| 30.65 | 2-thienyl | XXIII | N | NH |
| 30.66 | 3-thienyl | XXIII | N | NH |
| 30.67 | 2-pyridyl | XXIII | N | NH |
| 30.68 | 3-pyridyl | XXIII | N | NH |
| 30.69 | 5-pyrimidinyl | XXIII | N | NH |
| 30.70 | 2-napthyl | XXIII | N | NH |

As used in Tables 1 to 30 Ar is understood to be phenyl.

The compounds of Formula I are prepared in a three step sequence. Schemes A and B describes the preparation of compounds of the formula (I) where n=1 and m=0. The α,β unsaturated compounds (XXV I) can be prepared by conventional condensation techniques. For example Organic Reactions, Volume 16, describes the general aldol condensation and specifically the condensation of benzaldehydes with ketones. A hydroxybenzaldehdyde is condensed with a ketone, $RCOCH_2R_1$, which when $R_1$=H is a methyl ketone, provides the unsaturated intermediate XXVI'. Substituted hydroxybenzaldehyde such as ortho, meta or parahydroxybenzaldehyde provides three regioisomeric intermediates XXVI and XXVI'. A varietal of reaction conditions can be employed to prepare the enones (XXVI and XXVI') which are described in *Organic Reactions*, Volume 16, pp. 69–85. For example, a ketone is dissolved in a hydroxylic solvent, such as ethanol, to which is added dropwise a solution of the hydroxybenzaldehyde in an aqueous basic solution. The bases used can be alkali metal hydroxides, such as potassium or sodium hydroxide and the dropwise addition is conducted from 0° C. to 35° C. preferably at ambient temperature.

The intermediate enone XXVI' is reacted with hydrazine or a substituted hydrazine to provide the intermediate XXVII' pyrazolines. Typical preparation of pyrazolines from unsaturated enones by treatment with hydrazine (for Z=H) are described in Synthetic Commun, 25(12), 1877–1883 (1995); JACS 73, 3840 (1951); Indian J. Chem Soc Sect B 98–104 (1992) and J. Indian Chem Soc 643–644 (1993). For example, in JACS 73, 3840 (1951), styryl cyclopropyl ketone is reacted with aqueous hydrazine in 95% ethanol and stirred on a steam bath for 1 hour which after distillation gave the pyrazoline in 86% yield. Similarly in Synthetic Commun, 25(12), 1877–1883 (1995) chalcones are treated with hydrazine monohydrate and stirred at reflux in ethanol and gave the pyrazolines in >90% yield.

Typical preparation of N-phenylpyrazolines (when Z is phenyl) from unsaturated enones are described in Indian J. Chem Soc Sect B 98–104 (1992), J. Chem Res. Synop. 5, 168–169(1994) and Bull Soc. Chim Belg 707(1958). For example in J. Chem Res. Synop. 5, 168–169, a chalcone is treated with excess phenylhydrazine at reflux in ethanol to give the N-phenyl pyrazolines in 60–70% yield. Similarly, in Indian J. Chem Soc Sect B 98–104, an N-phenylpyazoline was formed in 88% yield by treatment of an unsaturated carbonyl compound with phenylhydrazine at reflux in the presence of glacial acetic acid.

The intermediate isoxazolines XXVIII' can prepared from enone XXVI' by reaction with hydroxylamine as described in Bull Soc. Chim Belg 96(4), 293 (1987) and in Collect Czech Chem. Conimun. 59, 247–252 (1994). Typically the enone is treated with an equimolar amount of hydroxylamine hydrochloride in 0.3M ethanolic sodium hydroxide and stirred at reflux for upto 10 hours and after neutralization with HCl the product isolated by filtration.

Preparation of the pyrazole XXIX' from intermediate pyrazoline XXVII' is described in J. Indian Chenm Soc. 64(7), 408 (1987) by oxidation with $MnO_2$ at room temperature. Typically the pyrazolines are shaken with $MnO_2$, 3.0 equivalents., in chloroform at room temperature for 2 hours and the pyrazoles are isolated by chromatography.

Preparation of the isoxazoles XXX' from intermediate isoxazoline XXVIII' is described in Synthesis 837 (1977) and Synth. Commun. 219 (1978). Typically a 3,5-disubstituted-isoxazoline in 10:1 benzene: dioxane is treated with γ $MnO_2$ (5.0 equivalents by weight) and stirred at reflux with azeoptropic removal of the water with a Dean Stark trap. The reaction is filtered through Celite and the remaining residue contains the isoxazole.

compounds of Table 28 of Formula XVII (wherein $R_1$=H). Alkylation of intermediate XXVIII' derived from ortho-hydroxybenzaldehdyde provides compounds of Table 28 of Formula XVIII (wherein $R_1$=H). Alkylation of intermediate XXVIII' derived from para-hydroxybenzaldehdyde provides compounds of Table 28 of Formula XVIII (wherein $R_1$=H).

Alkylation of pyrazole intermediate XXIX' derived from pyrazoline XXVII' provides compounds of Tables 24 to 26 of Formula XI, XII and XII (wherein $R_1$=H). Alkylation of intermediate isoxazole XXX' derived from isoxazoline XXVIII' provides compounds of Table 30 of Formula XXIII, XXIV and XXV (wherein $R_1$=H).

Compounds of formula I where A is CH and V is O are prepared by alkylation methyl E-α-(2-

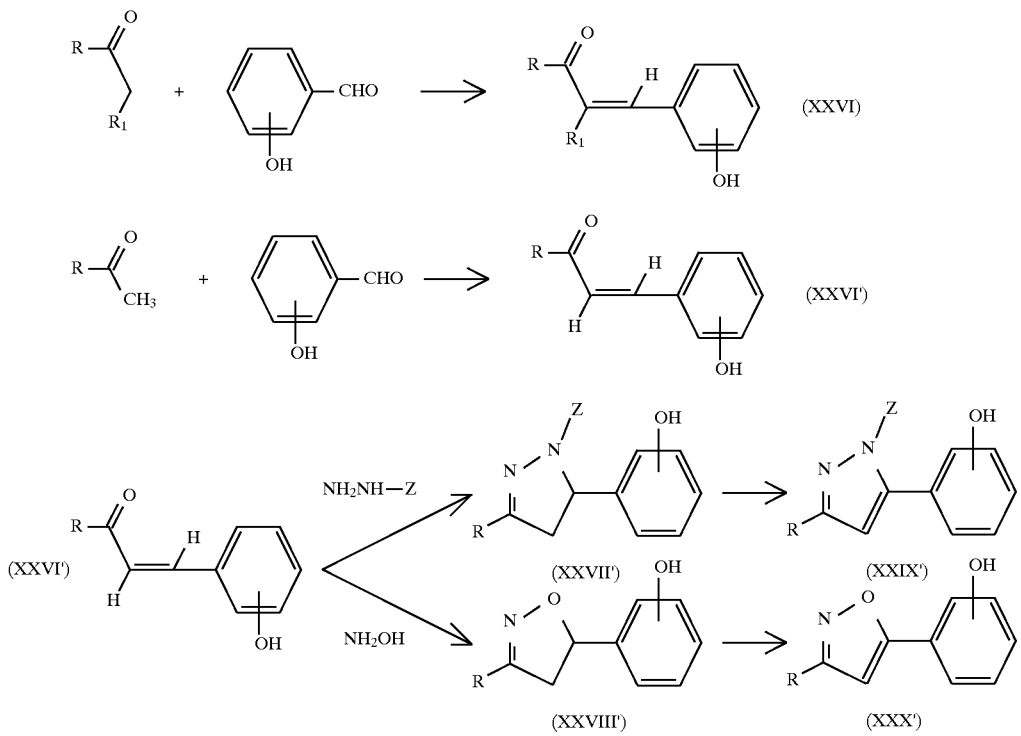

Scheme A:

Compounds of formula (V, VI, VII; XVII, XVIII, XIX; XI, XII, XIII and XXIII, XXIV, XXV) are prepared by the alkylation of intermediate pyrazoline XXVII' (when Z is not H), isoxazolines XXVIII', pyrazole XXIX' (when Z is not H) and isoxazole XXX, respectively, with the appropriately substituted benzyl bromides as shown in Scheme B.

When Z is H, the intermediates XXVII' and XXIX' are alkylated with Z—L, where L is halogen, and the resulting O,N dialkylated products are selectively O-dealkylated with HBr to provide intermediates XXVII' and XXIX' where Z is not H.

Alkylation of pyrazoline intermediate XXVII' derived from meta-hydroxybenzaldehyde provides compounds of Tables 11 to 20 of Formula V (wherein $R_1$=H). Alkylation of intermediate XXVII' derived from ortho-hydroxybenzaldehyde provides compounds of Tables 11–20 of Formula VI (wherein $R_1$=H). Alkylation of intermediate XXVII' derived from para-hydroxybenzaldehdyde provides compounds of Tables 11–20 of Formula VII (wherein $R_1$=H). Alkylation of isoxazoline intermediate XXVIII' derived from meta-hydroxyberzaldehdyde provides bromoomethylphenyl)-β-methoxyacrylate in the presence of a base such as a metal hydride, preferably NaH, in an aprotic solvent such as N,N-dimethyl-formamide. Methyl E-α-(2-bromomethylphenyl)-β-methoxyacrylate, as a single E isomer, can be prepared in two steps from 2-methylphenylacetate as described previously in U.S. Pat. No. 4,914,128, columns 3–4.

Compounds of formula I where A is N and V is oxygen are prepared by the reaction with methyl E-2-(bromomethyl) phenylglyoxylate O-methyloxime in the presence of a base such as a metal hydride, preferably NaH, in an aprotic solvent such as N,N dimethylformamide. Methyl 2-(bromnomethyl)phenylglyoxylate O-methyloxime can be prepared as described in U.S. Pat. Nos. 4,999,042, columns 17–18 and 5,157,144, columns 17–18. Methyl 2-(bromonmethyl)phenylglyoxalate O-methyloxime is prepared from methyl 2-methylphenylacetate by treatment with an alkyl nitrite under basic conditions to provide after methylation, methyl 2-methylphenylglyoxalate O-methyl oxime which can also be prepared from methyl 2-methylphenylglyoxalate by treatment with 2-hydroxylamine hydrochloride and methylation or by treatment with methoxylamine hydrochloride.

An alternative synthetic route to examples when A is N and V is oxygen, is provided by the alkylation with methyl 2-(bromomethyl)phenylglyoxylate followed by reaction with methoxylamine HCl or hydroxylamine HCl followed by methylation.

The amminolysis of oximinoacetates to oximinoacetamides has been described in U.S. Pat. Nos. 5,185,342, cols. 22, 48 and 57; 5,221,691, cols 26–27; and 5,407,902, col 8. Compounds of Formula (VI) where A is N and V is O are treated with 40% aqueous methylamine in methanol to provide compounds of Formula (V) where V is NH(CH$_3$). V and V' is reacted with N-methyl E-2-methoxyimino-2-[2-(bromomethyl)phenyl]acetamide in the presence of a base such as a metal hydride, preferably NaH, in an aprotic solvent such as dimethyl formide (DMF). N-methyl E-2-methoxyimino-2-[2-(bromomethyl)phenyl]acetamide is described in U.S. Pat. No. 5,387,714, col. 13.

Scheme B

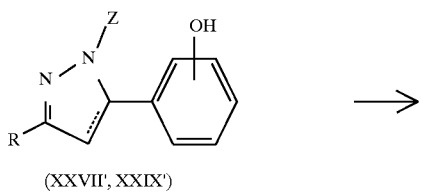

(XXVII', XXIX')

→

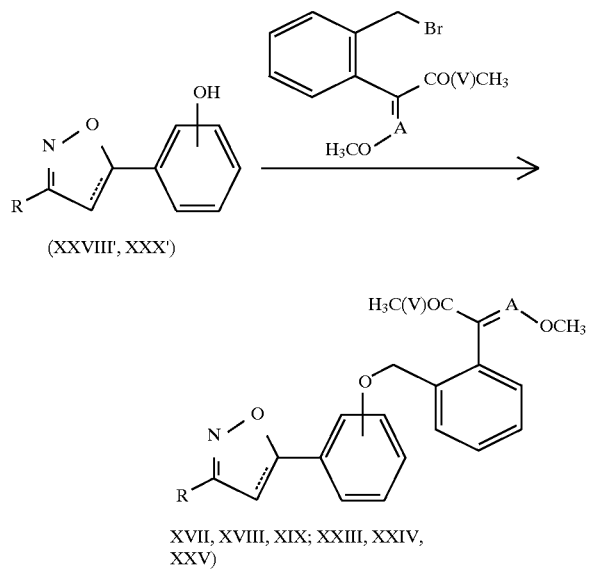

(XXVIII', XXX')

XVII, XVIII, XIX; XXIII, XXIV, XXV)

V, VI, VII; XI, XII, XIII

Scheme C describes the preparation of compounds of the formula (I) where n=0 and m=1. The α,β unsaturated compounds (XXXI) can be prepared by conventional condensation techniques. For example *Organic Reactions*, Volume 16 describes the general aldol condensation and specifically the condensation of aldehdydes with ketones. An aldehyde, for example a substituted benzaldehyde, is condensed with hydroxyphenylketones, (OH)ArCOCH2R$_1$, which when R$_1$=H is a methyl ketone to provide the unsaturated intermediate XXXI'.

Scheme C:

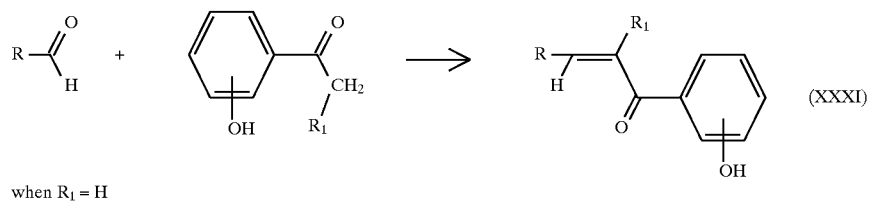

(XXXI)

when R$_1$ = H

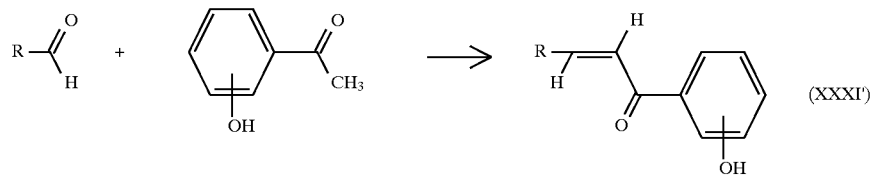

(XXXI')

-continued
Scheme C:

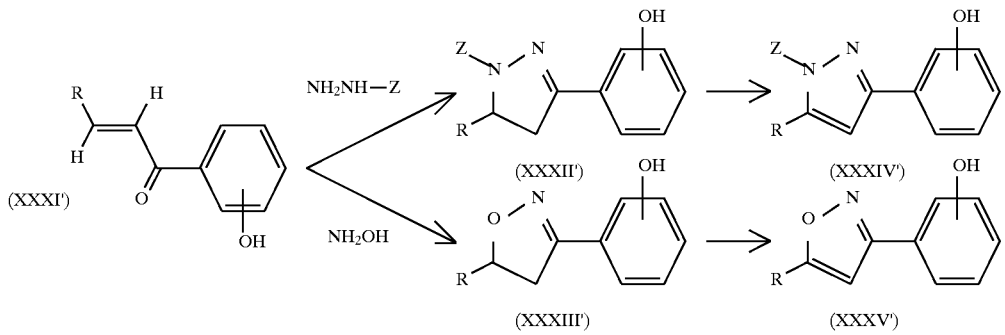

Substituted hydroxyphenylketones such as ortho, meta or para-hydroxyacetophenone provides three regioisomeric intermediates XXXI' where $R_1$=X=H. The intermediate enone XXXI' is reacted with hydrazine, substituted hydazines and hydroxylamine in the same manner as intermediate XXVI' (Scheme A). The pyrazoles XXIV' and the isoxazoles XXXV' are prepared by oxidation of the pyazoline XXXII" and isoxazoline XXXIII', respectively, in the same manner as described in Scheme A.

Compounds of formula (II, III, IV; VIII, IX, X; XIV, XV, XVI, and XX, XXI, XXII) are prepared by the alkylation of intermediate pyrazoline XXXII', isoxazolines XXXIII', pyrazole XXIV and XXXV, respectively, with the appropriately substituted benzyl bromides as shown in Scheme D.

Alkylation of pyrazoline intermediate XXXII' derived from meta-hydroxyacetophenone provides compounds of Tables 1 to 10 of Formula II (wherein $R_1$=H). Alkylation of isoxazoline intermediate XXXII' derived from ortho-acetophenone provides compounds of Tables 1 to 10 of Formula III (wherein $R_1$=H). Alkylation of intermediate XXXII' derived from para-hydroxyacetophenone provides compounds of Tables 1–10 of Formula IV (wherein $R_1$=H). Alkylation of intermediate XXXIII' derived from meta-hydroxyacetophenone provides compounds of Table 27 of Formula XIV (wherein $R_1$=H). Alkylation of intermediate XXXIII' derived from ortho-hydroxy-acetophenone provides compounds of Table 27 of Formula XV (wherein $R_1$=H). Alkylation of intermediate XXXIII' derived from para-hydroxyacetophenone provides compounds of Table 27 of Formula XVI (wherein $R_1$=H).

Alkylation of pyrazole intermediate XXXIV' derived from pyrazoline XXXII' provides compounds of Tables 21 to 23 of Formula VIII, IX and X (wherein $R_1$=H). Alkylation of intermediate isoxazole XXXV' derived from isoxazoline XXXIII' provides compounds of Table 29 of Fornmula XX, XXI and XXII (wherein $R_1$=H).

Scheme D.

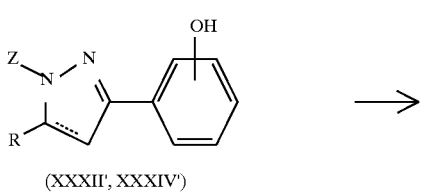

(XXXII', XXXIV')

-continued
Scheme D.

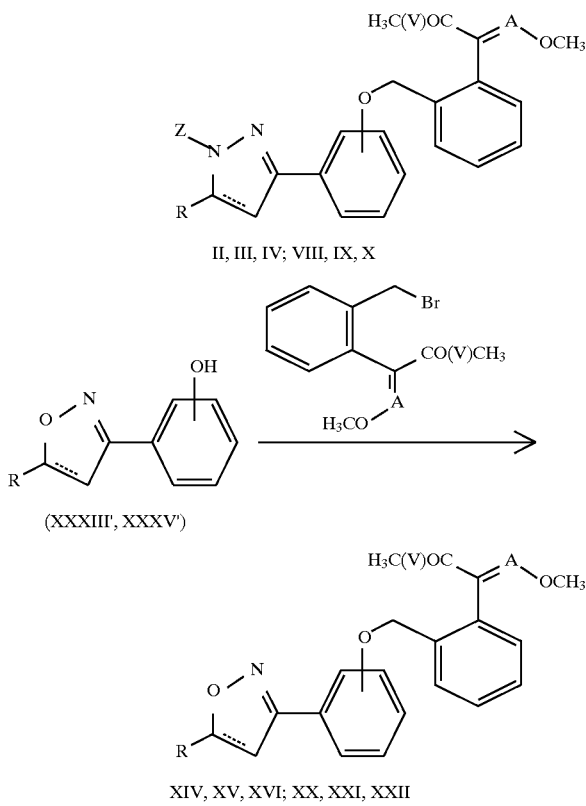

The compounds of this invention can be made according to the the following procedures:

EXAMPLE 1

Methyl 3-methoxy-2-[2-(3-(1-methyl-5-phenyl-2-pyrazolin-3-yl)phenoxymethyl)phenyl] propenoate (Compound 1.01, Table 1)

To a 25 ml vial, equipped with magnetic stirrer was charged 1.1 g (0.0045 moles) of 3-(3-hydroxylphenyl)-1n-methyl-5-phenyl-2-pyrazoline and 0.$^3$g (0.0045 moles) of powdered potassium hydroxide (85%), and 15 ml of dry N,N-dimethylformamide. To this solution was then added 1.3 g (0.0045 moles) of α-(2-(bromomethyl)phenyl)-β-methoxyacrylate. The vial was capped, and stirred overnight at ambient temperature. The contents were then poured into 100 ml of water and extracted with 2×100 ml of ethyl acetate. The organic extract was then washed with 2×100 ml of water and 100 ml of saturated aqueous sodium chloride solution. The organic extract was then dried over anhydrous magnesium sulfate, then filtered. The filtrated was concentrated under reduced pressure and the residue was chromatographed on a mixed bed of neutral alumina and silica gel with a 50% ethyl acetate, 50% hexane mobile phase. The pure fractions were combined and concentrated under reduced pressure, to afford 1.9 g of Methyl 3-methoxy-2-[2-(3-(1-methyl-5-phenyl-2-pyrazolin-3-yl)phenoxymethyl)phenyl] propenoate as an amber oil in 92% isolate yield.

H-NMR 200 MHz (CDCL$_3$): 2.9(s, 3H); 3.5(m, 2H); 3.7(s, 3H); 3.9(s, 3H); 4.1(m, 1H); 5.0(s, 2H); 6.9(m, 1H); 7.1–7.5(m, 12H); 7.6(s, 1H).

Preparation of 3-(3-hydroxyphenyl)-1-methyl-5-phenyl-2-pyrazoline from 3'-hydroxychalcone To a 100 ml round bottom flask equipped with a magnetic stirrer and reflux condenser was charged 1.0 g (0.0045 moles) of 3'-hydroxychalcone, and 25 mls of absolute ethanol. To this solution was then added 0.21 g (0.0045 moles) of methyl hydrazine in one portion. The reaction was then heated to reflux for two hours, then cooled. The solvent was removed under reduced pressure to afford 1.1 g of 3-(3-hydroxylphenyl)-1-methyl-5-phenyl-2-pyrazoline as a thick brown oil in 97% yield H-NMR 200 MHz (CDCL$_3$): 2.9(s, 3H); 3.0(t, 1H); 3.4(dd, 1H); 4.2(dd, 1H); 6.8–7.6(m, 9H); 11.0(br s, 1H).

EXAMPLE 2

Methyl 3-methoxy-2-[2-(3-(1-methyl-3-phenyl-2-pyrazolin-5-yl)phenoxymethyl)phenyl] propenoate (Compound 11.01, Table 11).

To a 25 ml vial, equipped with magnetic stirrer was charged 1.1 g (0.0045 moles) of the of 5-(3-hydroxyphenyl)-1-methyl-3-phenyl-2-pyrazoline, 0.3 g(0.0045 moles) of powdered potassium hydroxide (85%), and 15 ml of dry N,N-dimethylformamide. To this solution was then added 1.3 g (0.0045 moles) of α-(2-(bromomethyl)phenyl)-β-methoxyacrylate. The vial was capped, and stirred overnight at ambient temperature. The contents were then poured into 100 ml of water and extracted with 2×100 ml of ethyl acetate. The organic extract was then washed with 2×100 ml of water and 100 ml of saturated aqueous sodium chloride solution. The organic extract was then dried over anhydrous magnesium sulfate, then filtered. The filtrated was concentrated under reduced pressure and the residue was chromatographed on a mixed bed of neutral alumina and silica gel with a 50% ethyl acetate, 50% hexane mobile phase. The pure fractions were combined and concentrated under reduced pressure, to afford 1.8 g of Methyl 3-methoxy-2-[2-(3-(1-methyl-3-phenyl-2-pyrazolin-5-yl)phenoxymethyl)phenyl] propenoate as an amber oil in 88% isolated yield.

H-NMR 200 MHz (CDCL$_3$): 2.8(s, 3H); 3.0(t, 1H); 3.5 (m, 1H); 3.7(s, 3H); 3.9(s, 4.1(m, 1H); 5.0(s, 2H); 6.8(d,1H); 6.9(d, 1H); 7.1–7.8(m, 12H)

Preparation of 5-(3-hydroxyphenyl)-1-methyl-3-phenyl-2-pyrazoline from 3-hydroxychalcone To a 100 ml round bottom flask equipped with a magnetic stirrer and reflux condensor was charged 1.0 g (0.0045 moles) of 3-hydroxychalcone, and 25 mls of absolute ethanol. To this solution was then added 0.21 g (0.0045 moles) of methyl hydrazine in one portion. The reaction was then heated to reflux for two hours, then cooled. The solvent was removed under reduced pressure to afford 1.1 g of 5-(3-hydroxyphenyl)-1-methyl-3-phenyl-2-pyrazoline as a thick brown oil. 97% yield.

H-NMR 200 MHz (CDCL$_3$): 2.9(s, 3H); 3.0(t, 1H); 3.4(dd, 1H); 4.2(dd, 1H); 6.8–7.6(m, 9H); 11.0(bs, 1H)

EXAMPLE 3

Proton NMR data (200 MHz) are provided in Table 31 for typical examples of Tables 1 to 12 and are illustrative of the present invention.

TABLE 31

| Compound # | |
|---|---|
| 1.01 | 2.9(s, 3H); 3.5(m, 2H); 3.7(s, 3H); 3.9(s, 3H); 4.1(m, 1H); 5.0(s, 2H); 6.9(m, 1H); 7.1–7.5(m, 12H); 7.6(s, 1H) |
| 1.02 | 2.85(s, 3H); 3.3(m, 1H); 3.5(m, 1H); 3.7(s, 3H); 3.9(s, 3H); 4.1(m, 1H); 5.0(s, 2H); 6.8(d, 1H); 6.9(t, 1H); 7.1–7.5(m, 10H); 7.6(s, 1H); 7.8(d, 1H) |
| 1.03 | 2.8(s, 3H); 3.0(t, 1H); 3.5(m, 1H); 3.7(s, 3H); 3.9(s, 3H); 4.1(m, 1H); 5.0(s, 2H); 6.8(d, lH); 7.1(m, 1H); 7.2–7.7(m, 12H) |
| 1.57 | 3.2(m, 1H); 3.7(s, 3H); 3.9(s, 3H); 4.1(m, 1H); 5.0(s, 2H); 5.2(m, 1H); 6.8(d, 1H); 7.2–7.6(m, 15H); 7.7(s, 1H); 8.0(m, 1H) |
| 11.01 | 2.8(s, 3H); 3.0(t, 1H); 3.5(m, 1H); 3.7(s, 3H); 3.9(s, 3H); 4.1(m, 1H); 5.0(s, 2H); 6.8(d, 1H); 6.9(d, 1H); 7.1–7.8(m, 12H) |
| 11.02 | 2.8(m, 1H); 2.9(s, 3H); 3.6(m, 1H); 3.7(s, 3H); 3.9(s, 3H); 4.5(m, 1H); 5.0(s, 2H); 6.8(d, 1H); 6.9(t, 1H); 7.1–7.5(m, 7H); 7.6(m, 1H); 7.7(m, 4H) |
| 12.01 | 3.2(m, 1H); 3.7(s, 3H); 3.8(s, 3H); 3.9(m, 1H); 5.0(s, 2H); 5.2(m, 1H); 6.7(d, 1H); 6.9(m, 1H); 7.1–7.7(m, 14H); 7.8(s, 2H); 8.0(m, 1H) |
| 14.01 | 3.0(m, 1H); 3.4–3.6(m, 3H); 3.7(s, 3H); 3.9(s, 3H); 4.6(m, 1H); 5.0(s, 2H); 6.9(d, 1H); 7.0(m, 1H); 7.1–7.7(m, 12H) |

EXAMPLE 4

Numerous compounds of this invention were tested for fungicidal activity in vivo against the diseases described below. The compounds were dissolved in a 2:1:1 mixture of water, acetone and methanol (by volume), sprayed onto the plants, allowed to dry (one to two hours) and then the plants were inoculated with the fungus. Each test utilized control plants which were sprayed with the water, acetone and methanol mixture and inoculated with the fungus. The remainder of the technique of each of the tests is given below and the results for various compounds described herein by the Example number in Table 4 against the various fungi at a dose of 300 grams per hectare. The results are reported as percent disease control, compared to the control wherein) one hundred was rated as total disease control and zero was no disease control. The application of the fungi to the test plants was as follows:

Wheat Leaf Rust (WLR)

*Puccinia recondita* (f. sp. *tritici*) was cultured on 7 day old wheat (cultivar Fielder) over a 14 day period in the greenhouse. Spores were collected from the leaves by settling on aluminum foil. The spores were cleaned by sieving through a 250 micron opening screen and stored or used fresh. Storage employed sealed bags in an Ultralow freezer. A spore suspension was prepared from dry uredia by adding 20 mg (9.5 million spores) per mL of Soltrol oil. The suspension was dispensed into gelatin capsules (0.7 mL capacity) which attach to the oil atomizers. One capsule is used per of twenty of the 2 inch square pots of 7 day old Fielder wheat. After waiting for at least 15 minutes for the oil to evaporate from the wheat leaves, the plants were placed in a dark mist chamber (18°–20 20 C. and 100% relative humidity) for 24 hours. The plants were then put in the greenhouse for the latent period and scored after 10 days for disease levels. For protective tests the plants are inoculated one day after spraying the plants with the fungicide compounds.

Wheat Leaf Blotch (SNW)

*Septoria nodorum* was maintained on Czapek-Dox V-8 juice agar plates in an incubator in the dark at 20° C. for 48 to 72 hours, then incubated at 20° C. with alternating perios do 12 hours of light and 12 hours of darkness. A water suspension of the spores was obtained by shaking the portion of the plate with fungal material in deionized water and filtering through cheesecloth. The spore containing water suspension was diluted to a spore concentration of $3.0 \times 10^6$ spores per ml. The inoculum was dispersed by a DeVilbiss atomizer over one week old Fielder wheat plants which had been previously sprayed with the fungicide compound. The inoculated plants were placed in a humidity cabinet at 20° C. with alternating 12 hours of light and 12 hours of darkness for 96 hours. The inoculated seedlings were then moved to a controlled environment room at 20° C. for 8 days of incubation. Disease control values were recorded as percent control.

Wheat Powdery Mildew (WPM)

*Erysiphe graminis* (*f. sp. tritici*) was cultured on wheat seedlings in a controlled temperature room at 65 20 to 70 20 F. Mildew spores were shaken from the culture plants onto wheat seedlings which had been previously sprayed with the fungicide compound. The inoculated seedlings were kept in a controlled temperature room at 65 20 to 75 20 F. and subirrigated. The percent disease control was rated 8 to 10 days after the inoculation.

Cucumber Powdery Mildew (CPM)

*Sphaerotheca fulginea* was maintained on cucumber plants, cv. Bush Champion, in the greenhouse. Inoculum was prepared by washing the spores from the leaves with water which had 1 drop of Tween 80 per 100 ml. After shaking the plants, the inoculum was filtered through cheese cloth and misted onto the plants with a squirt bottle mister. The plants were then placed in the greenhouse for infection and incubation. The plants were scored seven days after inoculation. Disease control values were recorded as percent control.

Tomato Late Blight (TLB)

*Phytophthora infestans* was cultured on V8 juice plus $CaCO_3$ agar for three to four weeks. The spores were washed from the arag with water and sipsersed by DeVilbiss atomizer over the leaves of three week old Pixie tomato plants which had been sprayed previously with experimental fungicides. The inoculated plants were placed in a humidity cabinet at 20° C. for 24 hours for infection. The plants were then removed to a controlled environment room at 20° C. The plants were scored for disease control after five days.

Grape Downy Mildew (GDM)

*Plasmopara vticola* was maintained on leaves of live grape plants, cv. Delaware, in the controlled temperature chamber at 20° C. in humid air with moderate light intensity for 7 to 8 days. A water suspension of the spores from infested leaves was obtained and the spore concentration was adjusted to about $3 \times 10^5$ per ml of water. Delaware grape plants were inoculated by spraying the underside of leaves with a De Vilbiss atomizer until small drops were observed on the leaves. The inoculated plants were incubated in a mist chamber for 24 hours at 20° C. Disease control values were recorded as percent control seven days after inoculation.

When tested against cucumber powdery mildew at a dose of 300 grams per hectare, Examples 1.02, 11.02, 12.01, 14.01 exhibited 90% or better control.

When tested against septoria nodorum at 300 grams per hectare Examples 1.02, 11.01, 12.01, 14.01 exhibited 90% or better control.

At 300 grams per hectare Examples 1.01, 1.02, 11.01, 11.02, 12.01, 14.01 exhibited 90% or better control against wheat leaf rust.

At 300 grams per hectare Examples 1.01, 1.02, 12.01 exhibited 75% or better control against wheat powdery mildew At 300 grams/hectare, Examples 1.01, 1.02, 11.01, 11.02, 12.01, 14.01 exhibited 95% or better control against grape downy mildew.

The compounds of this invention are useful as agricultural fungicides and, as such, can be applied to various loci such as the seed, the soil or the foliage.

The compounds of this invention can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application, plants to be treated and diseases to be controlled. Generally, the compounds of this invention will be applied in amount of from about 0.005 kilogram to about 50 kilograms per hectare and preferably from about 0.025 to about 25 kilograms per hectare of the active ingredient.

As a seed protectant, the amount of toxicant coated on the seed is usually at a dosage rate of from about 0.05 to about 20, preferably from about 0.05 to about 4, and more preferably from about 0.1 to about 1 grams per hundred kilograms of seed. As a soil fungicide the chemical can be incorporated in the soil or applied to the surface usually at a rate of from about 0.02 to about 20, preferably from about 0.05 to about 10, and more preferably from about 0.1 to about 5 kilograms per hectare. As a foliar fungicide, the toxicant is usually applied to growing plants at a rate of from about 0.01 to about 10, preferably from about 0.02 to 5, and more preferably from about 0.25 to about 1 kilograms per hectare.

In as much as the compounds of this invention display fungicidal activity, these compounds can be combined with other known fungicides to provide broad spectrum activity. Suitable fungicides include, but are not limited to, those compounds listed in U.S. Pat. No. 5,252,594 (see in particular columns 14 and 15).

The compounds of this invention can be advantageously employed in various ways. Since these compounds possess broad spectrum fungicidal activity, they can be employed in the storage of cereal grain. These complexes can also be employed as fungicides in cereals including wheat, barley and rye, in rice, peanuts, beans and grapes, on turf, in fruit, nut and vegetable orchards, and for golf course applications.

Examples of diseases against which the compounds of the invention are useful include helminthosporium of corn and barley, wheat and barley powdery mildew, wheat leaf and stem rusts, tomato early blight, tonmato late blight, peanut early leaf spot, grape powdery mildew, serape black rot, apple scab, apple powdery mildew, cucumber powdery mildew, brown rot of fruits, botrytis, bean powdery mildew, cucumber anthracnose, wheat septoria nodorum, rice sheath blight and rice blast.

EXAMPLE 5

Numerous compounds of this invention were tested for insecticidal activity in vivo against the insects described below. The following test method was used to evaluate compounds of the present invention for insectidal activity. The compound to be evaluated was dissolved in an appropriate solvent, usually a mix of acetone, methanol and water, and sprayed over three excised leaf disks using a flat fan nozzle. After spraying, the leaf disks were allowed to dry. Two disks were infested with the leaf chewing insects (southern armyworm and Mexican bean beetle) and the third leaf disk was already infested with the two-spotted spider mite prior to spraying. The tested insect species were:

| AW | southern armyworm | *Spodoptera eridamia* |
|---|---|---|
| BB | Mexican bean beetle | *Epilachna varivestis* |
| MTA | two-spotted spider mite | *Teranychus uricate* |

Observations as percent control were made by visual inspection 24–48 hours after spraying.

When tested against Mexican bean beetle at 300 grams/hectare Examples 1.02, 11.01, 11.02, 12.01, 14.01 provided 50% or better control.

When tested against and two-spotted spider mite at 300 grams/hectare Examples 1.02, 1101, 14.01 provided 90% or better control.

The compositions and compounds of this invention can be applied directly to the locus to be protected, as for example, the area around or upon economic plants infected with insects or to plants on which infestation is to be prevented. Examples of injurious insects belong to the orders Lepidoptera, Coleoptera, Diptera, Thysanoptera, Hymenoptera, Heteroptera, Homoptera, Orthoptera, and Acarina. The compounds and compositions may be used either as contact or systemic pesticides. The compounds of the invention are applied to the insect's habitat at a rate of 0.0005 to 10 kilograms per hectare, preferably 0.05 to 5 and most preferably from 0.1 to 1 kilogram per hectare.

In the practice of the method of the invention, the active compound may be applied to the soil or foliage where it is absorbed by the plant, translocated to other plant parts and ultimately ingested by the pest or insects by means of ingestion of the plant part(s). This means of application is referred to as "systemic" application. Alternatively, the active compound may be applied to the soil and contacted therein with the insects and other pests to be controlled. This means of application is referred to as "soil" application. In another alternative, the active compound may be foliarly applied to the plants to be freed from insects and other pests which feed on the foliage.
Compositions and formulations according to the present invention may also include known pesticidal compounds. This expands the spectrum of activity of the preparation and may give rise to synergism. Suitable insecticides known in the art inlcude those listed in U.S. Pat. No. 5,075,471, see in particular columns 14 and 15.

The compounds of the present invention can be used in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations", (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier material or liquid carrier material, of the type usable in conventional pesticide compositions or formulations. By "agronomically acceptable carrier is meant any substance which can be used to dissolve, disperse of diffuse the active ingredient in the composition without impairing the active ingredients effectiveness and which by itself has no significant detrimental effect on the soil, equipment, desirable plants, or agronomic enviornment. If desired, adjuvants such as surfactants, stabilizers, antifoam agents and antidrift agents may also be combined.

Examples of compositions and lormulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles. Wettable powders, pastes, flowables and enulsifiable concentrates are concentrated preparations which are diluted with water before or during use. In such formulations, the compounds are extended with a liquid or solid carrier and, when desired, suitable surfactants are incorporated. Baits are preparations generally comprising a food or other substance attractive to insects, that includes at least one compound of the instantinvention.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art, and a discussion of adjuvants can be found in many references, such as in the John W. McCutcheon, Inc. publication "Detergents and Emulsifiers, Annual."

The active compounds of the present invention may be employed alone or in the form of mixtures with one another and/or with such solid and/or liquid dispersible carrier vehicles and/or witlh other known compatible active agents, especially plant protection agents, such as other insecticides, arthropodicides, nematicides, fungicides, bactericides, rodenticides, herbicides, fertilizers, growth regulating agents, synergists.

In the compositions of the invention, the active compound is present in an amount substantially between about 0.0001–99% by weight. For compositions suitable for storage or transportation, the amount of active ingredient is preferably between about 0.5–90% by weight, and more preferably between about 1–75% by weight of the mixture. Compositions suitable for direct application or field application generally contain the active compound in an amount substantially between about 0.0001–95%, preferably between about 0.0005–90% by weight, and more preferably between about 0.001–75% by weight of the mixture. The composition can also be stated as a ratio of the compound to the carrier. In the present invention the weight ratio of these materials (active compound/carrier) can vary from 99:1 to 1:4 and more preferably from 10:1 to 1:3.

In general, the compounds of this invention can be dissolved in certain solvents such as acetone, methanol, ethanol, dimethylformamide, pyridine or dimethyl sulfoxide and such solutions can be diluted with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent to enhance dispersion of the compound in water. The concentration of the active ingredient in emulsifiable concentrates is usually from about 10% to about 90%, and in flowable emulsion concentrates, can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 99%, preferably from about 40% to about 75%. A typical wettable powder is made by blending 50 parts of a pyridazinone, 45 parts of a synthetic precipitated hydrated silicon dioxide, such as that sold under the trademark Hi-SilR, and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silicoaluminate sold under the trademark Zeolex®7.

Dusts are prepared by mixing the compound of Formula I, or the enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The active compounds can be applied as insecticide sprays by methods commonly employed, such as conventional high-gallonage hydraulic sprays, low gallonage sprays, ultra-low-volume sprays, airblast spray, aerial sprays, and dusts.

The present invention also contemplates methods of killing, combatting or controlling pests which compromises contacting pests with a combative or toxic amount (i.e. a pesticidally effective amount) of at least one active compound of the invention alone or together with a carrier vehicle (composition or formulation) as noted above. The term "contacting" as employed in the specification and claims means applying to at least one of (a) such pests and (b) the corresponding habit at thereof (i.e., the locus to be protected, for example, to a growing crop or to an area where a crop is to be grown) the active compound of this invention alone or as a constituent of a composition or formulation.

In addition to the aforementioned ingredients the preparations according to the invention may also contain other substances commonly used in preparations of this kind. For example, a lubricant, such as calcium stearate or magnesium stearate, may be added to a wettable powder or to a mixture to be granulated. Furthermore there may, for example, be added "adhesives" such as polyvinylalcohol-cellulose derivatives or other colloidal materials, such as casein, to improve the adherence of the pesticide to the surface to be protected.

We claim:

1. A compound having the structure

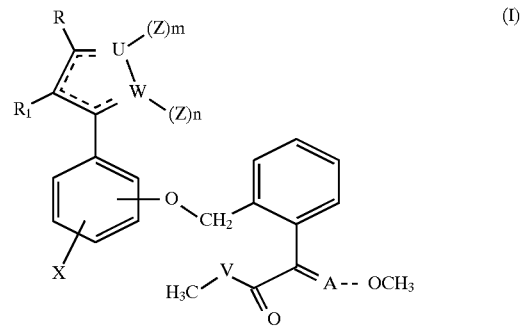

wherein A is N or CH; V is O or NH;
m and n are independently 0 and 1 provided that m+n is not 2, and U and W are independently O or N;
such that when U and W are both N and n is 0 and m is 1, the bond between the 1 and 5 atoms is a double bond and the bond between the $C_3$–$C_4$ atoms is a single or double bond, and when n is 1 and m is 0, the bond between the 2 and 3 atoms is a double bond and the bond between the $C_4$–$C_5$ atoms is a single or double bond;
and that when U is O and W is N and n=m=0, the bond between the 1 and 5 atoms is a double bond and the bond between the $C_3$–$C_4$ atoms is a single or double bond;
and that when U is N and W is O and n=m=0, the bond between the 2 and 3 atoms is a double bond and the bond between the $C_4$–$C_5$ atoms is a single or double bond;
X is independently selected from hydrogen, halo, ($C_1$–$C_4$) alkyl, and $C_1$–$C_4$)alkoxy;
R is independently selected from hydrogen, ($C_1$–$C_{12}$)alkyl, halo($C_1$–$C_{12}$)alkyl, ($C_2$–$C_8$)alkenyl, ($C_2$–$C_8$)alkynyl, ($C_1$–$C_{12}$)alkoxy($C_1$–$C_{12}$)alkyl, ($C_3$–$C_7$)cycloalkyl, ($C_3$–$C_7$)cycloalkyl($C_1$–$C_4$)alkyl, aryl, aralkyl, heterocyclic and
$R_1$ is independently selected from hydrogen, ($C_1$–$C_6$)alkyl, and aryl; and
Z is selected from ($C_1$–$C_6$)alkyl, halo($C_1$–$C_6$)alkyl, ($C_3$–$C_7$) cycloalkyl, ($C_3$–$C_7$)cycloalkyl($C_1$–$C_4$)alkyl, aryl and aralkyl.

2. The compound of claim 1 wherein A is CH.
3. The compound of claim 1 wherein A is N.
4. The compound of claim 2 wherein V is O.
5. The compound of claim 3 wherein V is O, NH.
6. The compound of claim 4 where the moiety

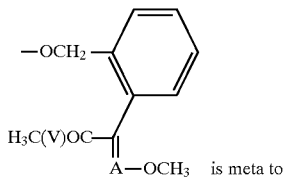

is meta to

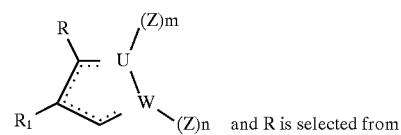

and R is selected from the group consisting of ($C_1$–$C_{12}$)alkyl, halo($C_1$–$C_{12}$)alkyl, monohalosubstitutedphenyl, ($C_1$–$C_4$)alkyl substituted phenyl, and trihalosubstituted phenyl.

7. The compound of claim 6 wherein U and W are N, $R_1$ is H, n=1 and m=0 and the bond between atoms 2 and 3 is a double bond.

8. The compound of claim 7 wherein Z is selected from $(C_1-C_6)$alkyl, phenyl, 3-halophenyl, 4-halophenyl and 4-$(C_1-C_4)$alkylphenyl.

9. The compound of claim 8 wherein R is selected from the group consisting of $(C_1-C_4)$alkyl, halo$(C_1-C_4)$alkyl, phenyl, 2-halophenyl, 3-halophenyl, 4-halophenyl, 2-$(C_1-C_4)$alkylphenyl, 3-$(C_1-C_4)$alkylphenyl and 4-$(C_1-C_4)$alkylphenyl.

10. The compound of claim 9 wherein R is selected from the group consisting of 2-fluorophenyl, 3-fluorophenyl, and 4-fluorophenyl.

11. The compound of claim 5 where the moiety

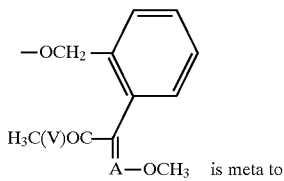

is meta to

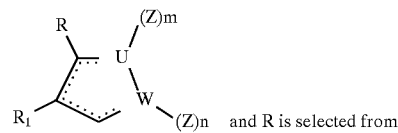

and R is selected from the group consisting of $(C_1-C_{12})$alkyl, halo$(C_1-C_{12})$alkyl, monohalosubstitutedphenyl, $(C_1-C_4)$alkyl substituted phenyl, and trihalosubstituted phenyl.

12. The compound of claim 11 wherein U and W are N, $R_1$ is H, n=1 and m=0 and the bond between the atoms 2 and 3 is a double bond.

13. The compound of claim 12 wherein Z is selected from $(C_1-C_6)$alkyl, phenyl, 3-halophenyl, 4-halophenyl and 4-$(C_1-C_4)$alkylphenyl.

14. The compound of claim 13 wherein R is selected from the group consisting of $(C_1-C_4)$alkyl, halo$(C_1-C_4)$alkyl, 2-halophenyl, 3-halophenyl, 4-halophenyl, 2-$(C_1-C_4)$alkylphenyl, 3-$(C_1-C_4)$alkylphenyl and 4-$(C_1-C_4)$alkylphenyl.

15. The compound of claim 14 wherein R is selected from the group consisting of 2-fluorophenyl, 3-fluorophenyl, and 4-fluorophenyl.

16. A fungicidal composition for controlling phytopathogenic fungi which comprises an agronomically acceptable carrier and the compound of claim 1 wherein the weight ratio of the carrier to the compound is 99:1 to 1:4.

17. The composition of claim 16 wherein the weight ratio of the agriculturally acceptable carrier to compound is 10:1 to 1:3.

18. A method for controlling phytophathogenic fungi which comprises applying to the locus of the seed, plant or soil the compound of claim 1 at a rate of from 0.005 to 50 kilograms per hectare.

19. The method of claim 18 wherein the compound of claim 1 is applied at the rate of from 0.025 to 10 kilograms per hectare.

20. A method for controlling insects in an area which comprises applying to the area the compound of claim 1 at a rate of 0.005 to 10 kilograms per hectare.

* * * * *